(12) United States Patent
Forte et al.

(10) Patent No.: US 10,043,415 B2
(45) Date of Patent: Aug. 7, 2018

(54) SYSTEM, METHOD AND COMPUTER PROGRAM FOR TRAINING FOR MEDICAL EXAMINATIONS INVOLVING MANIPULATION OF MEDICAL TOOLS

(71) Applicant: THE HOSPITAL FOR SICK CHILDREN, Toronto (CA)

(72) Inventors: Vito Forte, Toronto (CA); Bradley Hubbard, Toronto (CA); Brian Carrillo, Toronto (CA)

(73) Assignee: THE HOSPITAL FOR SICK CHILDREN, Toronto (CA)

( * ) Notice: Subject to any disclaimer, the term of this patent is extended or adjusted under 35 U.S.C. 154(b) by 505 days.

(21) Appl. No.: 14/426,411

(22) PCT Filed: Sep. 6, 2013

(86) PCT No.: PCT/CA2013/000762
§ 371 (c)(1),
(2) Date: Mar. 6, 2015

(87) PCT Pub. No.: WO2014/036639
PCT Pub. Date: Mar. 13, 2014

(65) Prior Publication Data
US 2015/0221236 A1    Aug. 6, 2015

Related U.S. Application Data

(60) Provisional application No. 61/698,122, filed on Sep. 7, 2012.

(51) Int. Cl.
GO9B 23/28    (2006.01)
GO9B 23/30    (2006.01)
(Continued)

(52) U.S. Cl.
CPC ............... G09B 23/28 (2013.01); G09B 5/02 (2013.01); G09B 23/285 (2013.01); G09B 23/30 (2013.01); G16H 50/50 (2018.01); A61B 1/227 (2013.01)

(58) Field of Classification Search
USPC .......................................................... 434/262
See application file for complete search history.

(56) References Cited

U.S. PATENT DOCUMENTS

2010/0248200 A1    9/2010 Ladak et al.

FOREIGN PATENT DOCUMENTS

WO    2012142697 A1    10/2012

OTHER PUBLICATIONS

WIPO, International Search Report and Written Opinion for PCT Application No. PCT/CA2013/000762 dated Nov. 8, 2013.
(Continued)

Primary Examiner — Kesha Frisby
(74) Attorney, Agent, or Firm — Norton Rose Fulbright Canada LLP

(57) ABSTRACT

The present invention is a medical training simulation apparatus and computer-implemented training method for training of medical professionals in medical examinations involving body parts with concealed geometry, such as in pneumatic otoscopy of the ear. A video adaptation tool is provided whereby one or more displayed images are adapted based on movements or sensor readings related to manipulation of a medical tool within a physical model of a body part. A computer system is also provided that includes at least one medical training simulation apparatus.

19 Claims, 13 Drawing Sheets

(51) Int. Cl.
*G09B 5/02* (2006.01)
*G16H 50/50* (2018.01)
*A61B 1/227* (2006.01)

(56) References Cited

OTHER PUBLICATIONS youtube.com, Otosim training video, Mar. 13, 2012. Available online at: https://www.youtube.com/watch?v=kZoexzOnaXg#t=12.
otosim.com, PneumatoSim™, 2012. Available online at: http://web.archive.org/web/20150216061622/http://otosim.com/pneumatic-otoscopy-trainer/.

SYSTEM, METHOD AND COMPUTER PROGRAM FOR TRAINING FOR MEDICAL EXAMINATIONS INVOLVING MANIPULATION OF MEDICAL TOOLS

PRIORITY

This application claims all benefit, including priority, of U.S. Provisional Patent Application Ser. No. 61/698,122, filed Sep. 7, 2012 entitled SYSTEM, METHOD AND COMPUTER PROGRAM FOR TRAINING FOR MEDICAL EXAMINATIONS INVOLVING MANIPULATION OF MEDICAL TOOLS.

FIELD OF THE INVENTION

The present invention relates to computer implemented training systems. The present invention more specifically relates to computer implemented training systems that simulate body parts to build skills pertaining to conducting medical examinations or procedures.

INTRODUCTION

Numerous medical examinations or procedures involve body parts with concealed anatomy, such as the ear, nose, throat or eye. These medical examinations or procedures generally involve the use of a specialized medical tool.

One example of such a medical examination is pneumatic otoscopy.

Pneumatic otoscopy examines the health of the ear drum (tympanic membrane) by modulation of (alternating negative and positive pressure) the pressure to the ear and observing the response (movement or lack thereof of the tympanic membrane). The tool used is a variation on an otoscope, called a pneumatic otoscope. A pneumatic otoscope generally consists of a standard otoscope including a bulb for modulation of the air pressure and an air passage at the end of the otoscope that communicates with the ear for application of the modulating air pressure to the tympanic membrane at the end of the outer ear canal. The pneumatic otoscope allows modulation of the air pressure and the viewing of the ear drum to discern movements. The pneumatic otoscope is designed to apply a modest vacuum (negative pressure) and positive pressure to the ear in order to determine whether there is fluid in the middle ear. If the ear drum moves this tends to suggest a healthy ear. The ear drum does not move if there is fluid in the middle ear. Small amounts of pressure are sufficient to move a healthy ear drum.

Otoscopes generally consist of a handle and a head. The head contains a light source and a simple low-power magnifying lens, typically around 8 diopters. The distal (front) end of the otoscope has an attachment for disposable plastic ear specula. The examiner first straightens the ear canal by pulling on the pinna and then inserts the ear speculum side of the otoscope into the external ear. It is important to brace the hand holding the otoscope against the patient's head to avoid injury to the ear canal by placing the index finger or little finger against the head. The examiner can then look through a lens on the rear of the instrument and see inside the ear canal.

Medical professionals need to learn to (A) to apply the correct amount of pressure. Too much pressure is uncomfortable for the patient, and can hurt the ear drum. Moving the ear drum using vacuum/pressure optimally involves the application of a spectrum of pressure (modulation of pressure) using a pneumatic otoscopy tool. Learning to use the pneumatic otoscopy tool to generate the correct spectrum of pressure can take some practice. Importantly, in order to generate the correct spectrum of pressure, a seal of the ear must be generated using the tool. The failure to generate this seal is a common mistake resulting in an ineffective examination. Medical professionals need to be trained to create this seal, and to do so correctly. Also, (B) the medical professional needs to learn what to look for inside a patient's ear. The appearance of the inside of an ear can vary, and therefore so can the appearance of what constitutes a healthy or unhealthy ear.

At most medical schools, training in medical examinations or procedures relating to body parts with concealed anatomy involves visual identification of possible defects or medical conditions. The training is generally conducted through the use of basic tools, such as slide presentations including photos of the physical defects or medical conditions. Some estimate that only around five percent of medical students feel comfortable about their skills to use specialized medical tools, for example, such as with their otology skills, at the end of their residency.

Some prior art medical training systems are known. For example, the "NASCOLIFEFORM", and United States Publication No. 2008/0050710 both include a model of a head or portion of a head, which contains an area that can receive one of a plurality of inserts that simulate an ear and also the ear canal. Such inserts are formed so that the inside of the model of the ear canal shows a physical defect or medical condition. The inserts are generally made of a flexible material such that trainees may pull on the ear portion thus also displacing the ear canal as is required in otoscopy examinations.

As another example, U.S. Pat. No. 6,241,526, issued to Auran et al., discloses a device for training physicians in tympanocentesis. The device includes an outer member resembling a side profile of a child's head and shoulder area. The outer member is attached to a surface portion to define a receiving area for receiving a slidable inner member or insert. A replica of at least an eardrum and an ear canal of a child's inner ear are associated with the sliding inner member. A training portion of the inner member supports a simulated inner ear, positions the simulated inner ear to a desired position adjacent the outer ear of the outer member, and acts as a holder for the training cartridges used with the training device. The cartridges or inserts simulate the "look and feel" of popping through the tympanic membrane. The cartridges include one or more training areas. The disclosed prior art invention trains the user in proper location and depth. Once all of the training areas of the cartridge have been used, it is replaced with a new cartridge.

There are several drawbacks to the prior art training systems. For example, the trainer cannot see the image of the physical defect or medical condition at the same time as it is shown to the trainee. Another drawback is that manual changing of the ear inserts is required for the prior art system. Yet another drawback is that, because of cost, the number of inserts is often limited in prior art systems. The limited number of inserts can reduce the number of video content objects of physical defects or medical conditions to which the trainees are exposed through use of the training system.

SUMMARY

In one aspect of the invention, a computer implemented medical training method is provided comprising: (A) one or more users engaging a simulation computer system to initiate a medical training routine, by means of one or more computer processors, the simulation computer system including a video display, and a controller for controlling the video display that displays one or more medical images; (B) each of the one or more users inserting a medical tool into an opening defined by an physical model of a body part that is part of, or linked to, the simulation system; and (C) the one or more users using the medical examination tool, and moving the medical examination tool, through the physical model, so as to view an interior defined by the simulation system that simulates the concealed anatomy of the body part by optically altering the one or more images so as to simulate the appearance of the interior of the body part when viewed using the medical tool, including by: (i) tracking movement of the medical examination tool; and (ii) dynamically adapting the one or more images displayed by the video display based on the tracked movements of the medical examination tool so as to simulate appearance of the interior of the body part when moving the medical examination tool in connection with conducting the medical examination on a human subject.

In another aspect of the invention, a medical training apparatus is provided comprising: (A) one or more physical models of a body part consecutively attachable to a base unit of the medical training apparatus, each physical model including an opening and defining a structure that simulates concealed geometry of said body part, said opening being configured to enable a trainee to insert a medical tool therein; (B) a modified medical tool that is linked to the base unit; (C) a video display that is part of the base unit, controllable to display a series of medical images relating to the body part; (D) a means for altering the series of images such that its appearance simulates the appearance of the content of the image within the concealed geometry within the body part when viewed using the medical tool inserted in the physical model; and (E) means for tracking movement of the medical tool, and dynamically adapting the one or more images displayed by the video display based on the tracked movements of the medical examination tool so as to simulate appearance of the interior of the body part when moving the medical examination tool in connection with conducting the medical examination on a human subject; said medical training apparatus being operable to achieve a simulation for training the trainee to: manipulate the medical tool within the body part of the physical model; and identify the condition within the concealed geometry of the body part of the one of the one or more physical models attached to the medical training apparatus.

In another aspect of the invention, the medical images consist of one or more groups of images, wherein each group of images depict the concealed geometry of the body part across a medical examination involving movements of the medical tool, where individual images are indexed to particular movements of the medical tool; the medical training apparatus further comprises a video adaptation component that is configured to receive iteratively input from the means for tracking movement ("movement tracker"), and to dynamically retrieve the images that correspond to the tracked movements, and thereby display a sequence of images from the group of images that correspond to the user's movements made in using the medical tool in connection with conducting the medical examination on a human subject.

In a still other aspect of the invention: (A) the medical examination tool is a pneumatic otoscope; (B) the medical training apparatus includes a pressure sensor unit that tracks the modulation of pressure by the user using a bulb of a pneumatic otoscope so as to generate a series of pressure values; and (C) the pressure values are provided to the video adaptation component as input, and based on this input the video adaptation component dynamically retrieves and displays a sequence of images from the group of images that correspond to the user's use of the bulb, thereby simulating the variation of the appearance of the interior of an ear in conjunction with the particular modulation of pressure applied by the user.

In yet another aspect of the invention, a computer network enabled medical training computer system is provided comprising: one or more medical training apparatuses of the present invention; and one or more computers linked to one or more medical training apparatuses, each of the one or more computers incorporating one or more computer processors configured to operate a computer program, said computer program being operable to control a medical training module and control the video display and the display of the groups of images for the purpose of training the one or more trainees.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The present invention enables the provision of such instruction and permits users to practice examination in an effective manner. The system, computer program, and method of the invention represent a significant advancement of the art, and provide a practical and cost effective system for broader dissemination of such instruction and/or practice.

In one aspect, a medical training system for simulating pneumatic otoscopy is provided comprising: (A) a computer system linked to at least one base unit; (B) the base unit including or receiving one or more physical models of an outside of an ear, the physical model including an opening, and the base unit including one or more components that define a structure that simulates concealed geometry of the ear, the opening being configured to enable a trainee to insert a pneumatic otoscope through the opening and into the structure, the pneumatic otoscope including a lens and an apparatus for applying pressure to the inside of the ear (pressure applicator); (C) the one or more components including a video display that is controllable by the computer system, using a video controller, to display a series of medical images relating to the inside of an ear, such that when the trainee looks through the lens of the pneumatic otoscope, viewing the interior of the structure through the lens simulates the appearance of the interior of the ear; and (D) a tracker that tracks movements of the pneumatic otoscope made by the trainee, including movements of the pressure applicator, the tracker providing information to the video controller so as to dynamically adapt the one or more images displayed by the video display based on the tracked movements of the pneumatic otoscope, so as to simulate appearance of the interior of the ear when operating the pneumatic otoscope in conduct an ear examination, including using the pressure applicator.

In another aspect, the one or more medical images include images that show a tympanic membrane of an ear drum in different states based on application of pressure using a pneumatic otoscope. In yet another aspect, the system is configured to train the trainee to generate a correct spectrum of pressure to test the mobility of the tympanic membrane of the ear drum, without harming a patient.

In another aspect, the one or more images include images of the inside of an ear presenting a medical condition, and the medical training system is configured to train the trainee to identify the condition using a pneumatic otoscope.

In another aspect, the medical images consist of one or more groups of images, wherein each group of images depicts the concealed geometry of an ear across a series of movements involved in conducting an examination using a pneumatic otoscope, wherein individual images are indexed to particular movements of the pneumatic otoscope in connection with an ear examination using the pneumatic otoscope, and wherein the group of images represents the appearance of an ear across a spectrum of pressure generated using the pressure applicator; and the tracker sends information to the computer system, and in response the computer system iteratively retrieves and directs the video controller to display the image corresponding to a particular movement tracked by the tracker, such that across a series of iterations, a series of images are displayed that simulate the appearance of the interior of the ear based on the particular movements of the trainee using the pneumatic otoscope in connection with conducting an ear examination on a human subject.

In another aspect, each medical image includes a frame, and each frame is mapped to a pressure value within a range of defined pressure, wherein based on pressure expressed using the pressure applicator, and sensed by the pressure sensor unit, a real time or near real time pressure value is identified (based on use of the pneumatic otoscope by the trainee in connection with an ear examination using the pneumatic otoscope) and the corresponding frame is retrieved and displayed by the video display.

In another aspect, a medical training system is provided wherein one or more base units are networked; and one or more computer systems execute programming that include an ear examination training module, wherein the ear examination training module may be used to control the images displayed on the respective video displays of the one or more base units.

In another aspect of the medical training system, a trainer module is executed by the one or more computer systems, and the trainer module selectively controls the images displayed by the respective one or more base units, including based on one or more pneumatic otoscopy lesson modules, and the one or more of the base units include a monitoring module that is used to monitor the performance of trainee(s) using each base unit, and associated performance data is logged by the trainer module for trainee assessment and reporting.

In another aspect, a computer implemented medical training method for learning to conduct a medical examination using a pneumatic otoscope is provided comprising: (A) one or more users engaging a simulation computer system to initiate an ear examination training routine, by means of one or more computer processors, the simulation computer system including: a video display disposed within a base unit that includes a physical model of an outside of an ear, the physical model including an opening, and the base unit including one or more components that define a structure that simulates concealed geometry of the ear; a pneumatic otoscope including a lens and a pressure applicator; a database including a series of medical images that show the inside of an ear, where each image corresponds to the appearance of the inside of an ear in connection application of particular pressure using the pressure applicator; and a controller for controlling the video display to selective display the medical images; wherein, the opening is configured to enable a trainee to insert a pneumatic otoscope through the opening and into the structure, and view an interior of the structure through the lens; (B) one or more of the users who are trainee users inserting the pneumatic otoscope into the opening, and using the pressure applicator so as to apply pressure as is done in conducting an ear examination using a pneumatic otoscope; (C) tracking the pressure applied using the pressure applicator based on a series of pressure values; (D) selectively retrieving and displaying to the video display medical images corresponding to the series of pressure values, thereby simulating the appearance of the interior of the ear during an ear examination when the trainee users view the interior of the structure through the lens.

In another aspect of the method, the method includes generating a feedback message based on the performance of a trainee user based on one or more training parameters. In another aspect, the method includes communicating feedback information to a trainee user based on their performance relative to the training parameters.

BRIEF DESCRIPTION OF THE DRAWINGS

The invention will be better understood and objects of the invention will become apparent when consideration is given to the following detailed description thereof. Such description makes reference to the annexed drawings wherein.

Figure 1A:
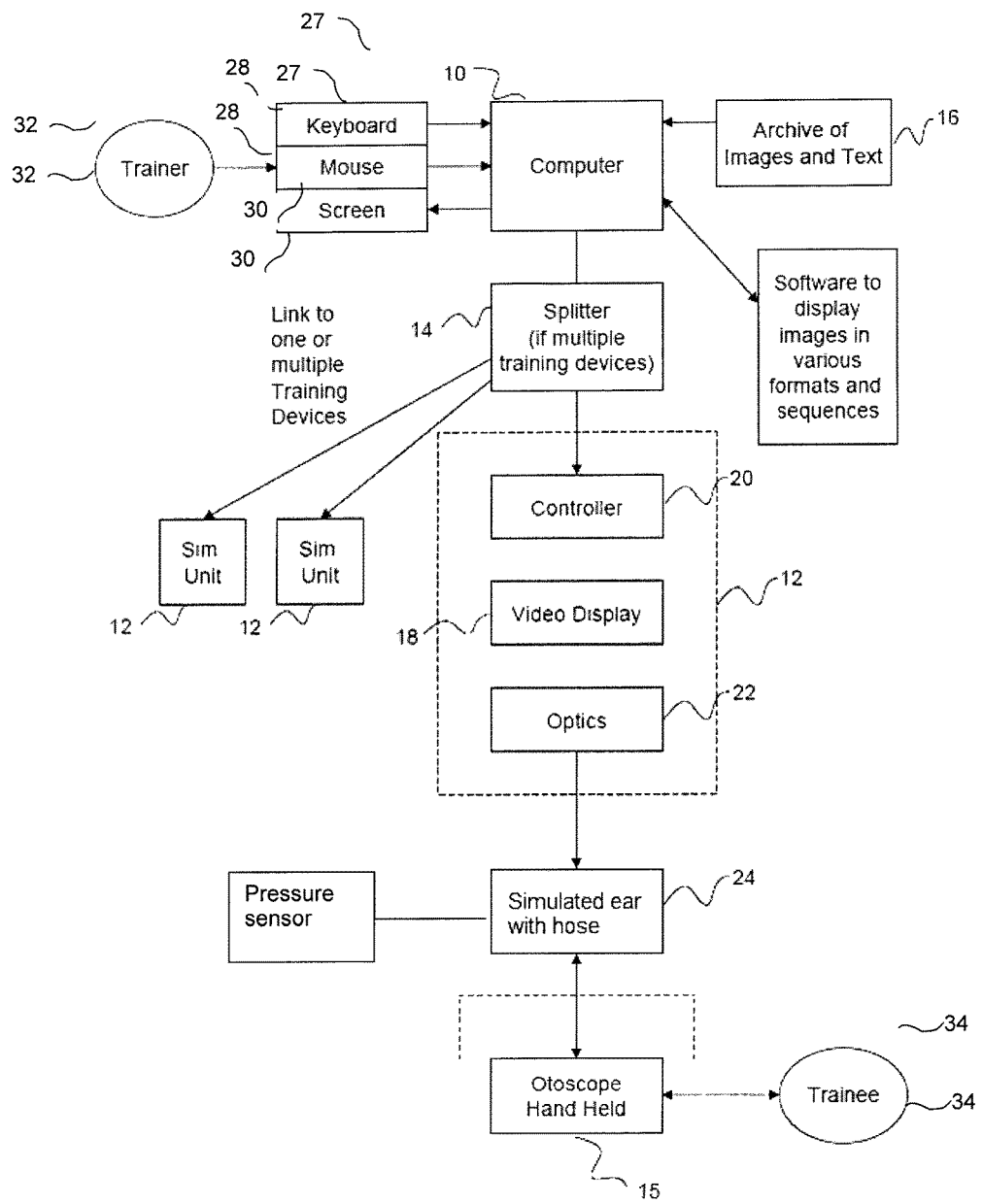
FIG. 1a is a system diagram of one embodiment of the present invention, adapted for pneumatic otoscopy.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE INVENTION

The invention is a medical training simulation apparatus, system and computer product that includes: (A) a physical model of a body part of a human or animal that has concealed anatomy (for example the concealed anatomy may be because of an orifice such as an ear canal, nose, throat, or may be other types of concealed anatomy, such as the concealed anatomy of an eye), and that is adapted to receive a medical examination tool; (B) a video viewer that simulates the viewing of the concealed anatomy using the medical examination tool by (i) receiving input from the medical examination tool, and (ii) adjusting a sequence of video frames to correspond to the input from the medical examination tool.

The proper use of a medical examination tool may require the manipulation of the medical examination tool, and this manipulation may correspond into the viewing of the human anatomy using the medical examination tool. Learning to use the medical examination tool may require learning the specific impact on the human anatomy of the use of the medical examination tool.

For example as stated before: (A) in connection with pneumatic otoscopy, the medical professional must learn (i) to create a proper seal, and (ii) apply the correct amount of vacuum/pressure. In one aspect, the medical professional must learn the relationships between their manipulation of the medical examination tool and the viewing of the human anatomy.

In one aspect of the invention, a video viewer and associated computer implemented method is provided that includes a novel and innovative video segmentation mechanism, which is described in detail below.

In embodiments of the present invention, there may be several physical models of various body parts provided as part of the medical training simulation apparatus. The physical models may each be used individually with the video viewer. For example, a physical model that is an ear body part may be used with the viewer at one point and then be removed and replaced with another physical model for another body part, such as a nose. In this manner the multiple physical models allow the medical training simulation apparatus to be used for training pertaining to: (a) the use of multiple specialized medical examination tools; and (b) multiple of body parts.

Figure 1B:
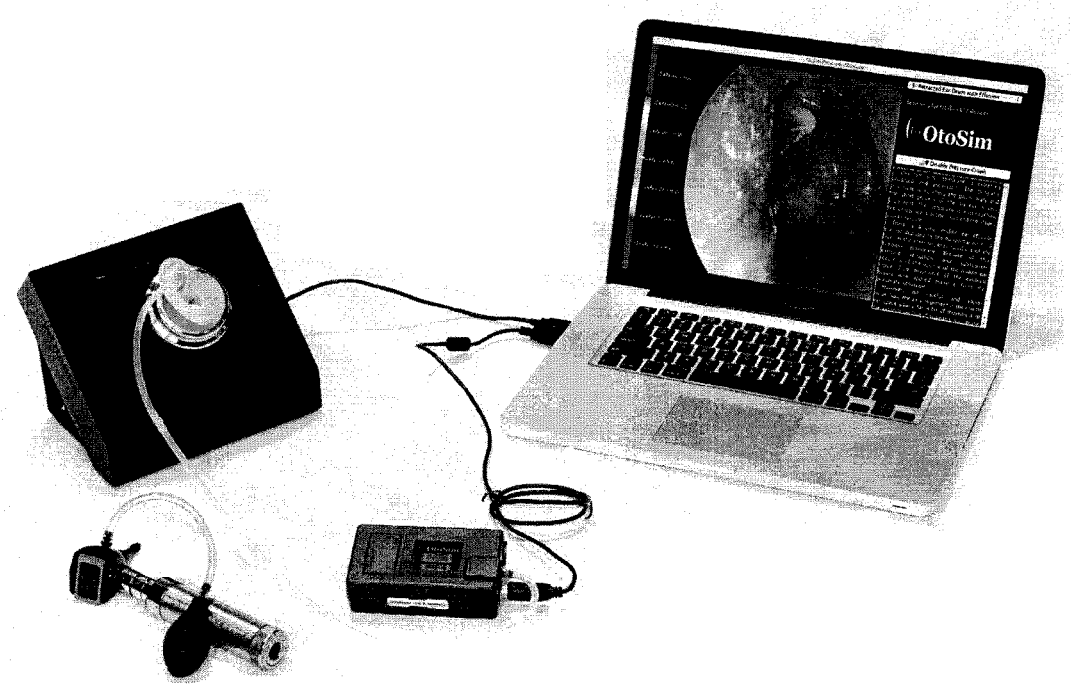
FIG. 1b is a photograph of a possible pneumatic otoscopy application of the present invention.

One particular embodiment relates to a system and an apparatus for simulating pneumatic otoscopy. FIG. 1a is a system diagram illustrating a possible computer system implementation of the present invention. FIG. 1b is a photograph of a possible implementation of the system and apparatus of the present invention. The photograph shows (A) a computer on which the computer program of the present invention is loaded, the computer being linked to (B) a base unit (that includes the optics and viewer described above, and a model of an ear), (C) a pressure sensor unit, where a tube connects the pressure sensor unit to the base unit, and (D) a pneumatic otoscope.

FIGS. 3 to 7f illustrate possible embodiments of the base system of the present invention. The base system is also described in related PCT Application CA2012/000359.

The present invention may be utilized to train trainees, for example medical professionals, to accurately conduct medical examinations (including to detect physical defects or medical conditions) while using specialized medical tools to investigate concealed anatomy. Body parts with concealed anatomy can represent difficult diagnostic environments. It is therefore important for medical practitioner trainees to learn to navigate within body parts with concealed anatomy environments. Navigation within such body parts requires learning to manipulate a specialized medical tool within the concealed anatomy, for example, such as an orifice defined by the body part with concealed anatomy, and learn the impact of their manipulation of the specialized medical tool on the viewing of the body part with concealed anatomy.

Moreover in connection with the present invention, the use of pneumatic otoscope involves the application of vacuum/pressure, which has an impact on the concealed anatomy of the ear (possible movement of the ear drum).

The present invention is operable to allow a trainee to learn to use these aspects to manipulate a medical tool, and navigate within a body part with concealed anatomy, which is represented by the physical model element of the present invention. As an example, if the concealed body part represented by the physical model of an implementation of embodiment of the present invention is an ear, the trainee can utilize the present invention to learn to manipulate a pneumatic otoscope and learn to observe the results of manipulation of the pneumatic otoscope on an ear canal.

In order to provide robust training to trainees, the video viewer of the training system of the present invention may provide ready access to a sequence of video content objects showing the relevant body part across one or more manipulations by the trainee of the medical tool. The trainee can therefore view a representation of a physical defect or medical condition relating to a particular body part through a medical tool and in the environment of the body part, which is provided by the physical model element of the present invention. In this manner, the present invention is operable to train a trainee to learn how physical defects or medical conditions will appear specifically within the environment of a body part when viewed through a medical tool, and in connection with one or more manipulations by the trainee of the medical tool. This allows medical practitioners to learn to be able to identify such physical defects or medical conditions in difficult diagnostic environments, and while manipulating the medical tools.

The present invention represents benefits and advantages over the prior art. For example, prior art training techniques are not generally effective in training medical professionals to navigate effectively within concealed anatomy, for example, such as concealed anatomy of an ear. In the case of pneumatic otoscopy for example, trainees can inflict discomfort or pain upon patients if they are not well trained in manipulation of a pneumatic otoscope within the concealed anatomy of an ear before using an otoscope on a patient. Also it can take time to learn to manipulate a pneumatic otoscope properly. Using live subjects to learn to use the relevant medical tools may not be practical. Therefore there is a need for a system that simulates body parts with concealed anatomy in a way that provides effective instruction. Designing a system with these characteristics requires significant innovation.

Prior art systems further fail to simulate the environment within which a medical tool is to be manipulated and other aspects of a medical examination. The present invention offers a benefit in that it is a training apparatus and system that both simulates the environment within which a medical tool is manipulated in connection with a medical examination or procedure conducted for a body part with concealed anatomy.

The present invention further provides ready access to video content that shows the body part in question in conjunction with the manipulations referred to. The video content is presented in a way that simulates the appearance of the body part with concealed geometry, using the medical tool in question, and upon the medical professional manipulating the medical tool in the same way as when engaging in a training module using the system of the present invention.

This enables the trainee to learn to manipulate a medical tool within a body part with concealed anatomy and to accurately identify a physical defect or medical condition in a simulated environment that closely resembles the environment of a live subject patient.

Additionally, the present invention is a training system and apparatus that is simple to use and cost effective. Prior art training systems are not simple to use, nor cost effective, and therefore this represents yet another benefit of the present invention over the prior art. That the present invention is simple to use and cost effective represent aspects that cause the present invention to be utilizable in a variety of medical training environments by a variety of medical trainees.

The present invention may be made widely available and accessible for purposes of training medical practitioners. Training using the present invention may have the outcome that discomfort, pain or injury to patients is avoided because training occurs before the medical professional conducts an examination of a patient. The present invention may further improve the ability of medical professionals who have used the training system to accurately identify relevant physical defects or medical conditions existing in concealed anatomy of a body part, and thereby improve the effectiveness and efficiency of diagnosis of such defects and conditions.

In embodiments of the present invention, the medical training simulation apparatus and system may be configured to enable a human user of the present invention to use a medical examination tool in relation to the physical model. The use of a medical tool in relation to a body part is required in a medical examination of the body part. Therefore, the present invention simulates a medical examination of a body part. The trainee may view one or more video content objects relating to physical defects or medical conditions affecting that body part in a way that simulates the appearance of such defects or conditions as they would be viewed during a medical examination of a live patient. Therefore, the present invention is operable to simulate the whole of the experience of a medical examination as experienced by a medical professional, including use of a medical tool, manipulation of the medical tool in a body part, viewing of a physical defect or medical condition in the body party (which generally involves viewing through the medical tool), and identification of the defect or condition.

The present invention may include physical models that represent body parts of humans or animal subjects. The viewer may further provide video content objects relating to the body part of a human or an animal, and relevant physical defects of medical conditions of that body part of a human or animal. Therefore, the present invention may be used to train a trainee in a simulated environment relevant to a human or animal subject. A skilled reader will recognize the variety of physical models and video content objects viewable using the video viewer that may be incorporated in the present invention and the multiple environments that may be simulated by the present invention for training purposes.

The present invention offers still another benefit over prior art solutions in that it provides a training apparatus and system operable to enable highly effective medical training. The effectiveness of the training of the present invention is in part due to the operability of the present invention to enable the user to use the appropriate medical examination tool in relation to the physical model which represents the appropriate anatomy. The effectiveness of the present invention is also related to the operability of the present invention to display one or more video content objects of physical defects or medical conditions relevant to the physical model integrated through a connection to present invention. The video content objects are provided in the present invention so that the physical model and video viewer in combination simulate real life anatomical geometry. The overall presentation of the present invention simulates the use of a medical tool in a body part and view through the medical tool of in relation to the body part in a human or animal subject. Prior art training systems do not offer the simulation environment offered by the present invention.

Thus, the medical training simulation apparatus and system of the present invention provides a significant advancement over the prior art. The present invention provides access to a significant number of video content objects of physical defects or medical conditions relevant to a body part in the environment of the body part. The present invention is further cost effective and therefore accessible to a significant proportion of medical professional trainees. The present invention, therefore, can play a role in providing access to important medical training that the prior art cannot achieve.

In one embodiment of the present invention, a medical training system may be provided that includes one or more combinations of the physical model and the video viewer of the present invention, which are connected together to form a medical training simulation apparatus, and a further connection from each combination of physical mode and the video viewer, by a wired or wireless means, to one or more computers. At least one of the one or more computers may be operable by a trainer. The trainer may utilize at least one of the one or more computers to guide one or more trainees working at one medical training simulation apparatus through one or more training sessions. The computer or computers operated by the trainer may be configured as required for the trainer to provide training to the trainees.

In such an embodiment, each trainee may have access to a medical training simulation apparatus that is connected to a medical training computer program by way of a server, computer or other means. The medical training computer program may be operable to initiate one or more medical training routines. The medical training routines may control one or more of the medical training simulation apparatuses that are linked to the medical training computer program. A trainer may operate the medical training computer program, and thereby control the medical training routine provided to the medical training simulation apparatus.

The medical training simulation apparatus utilized by a trainee may be located remotely from the computer or other means operating the medical training computer program that is controlled by the trainer. Thus, the trainee and trainer may be distantly located from one another. Alternatively, the trainee and the trainer may be closely located to one another. A skilled reader will recognize that variety of methods of configuring the apparatus and the computer or other means controlling the medical training computer program so that these elements are closely or remotely located from each other, for example, such as the incorporation of connections to one or more servers, the incorporation of an Internet connection, the incorporation of a cloud computing element, or other means.

The medical training computer program may be operable to enable one or more medical professional trainers to guide one or more trainees. A medical training simulation apparatus must be accessible to each of the one or more trainees. Each trainer may utilize the medical training computer program to guide one or more trainees through one or more medical training routines for which each trainee uses his or her medical training simulation apparatus. Thus, each trainer may train one or more trainees, and multiple groupings of trainee(s) and trainer may exist. Each grouping of trainee(s) and trainer may utilize the medical training computer program to operate different medical training routines, or the same medical training routine, but at a different pace. Thus, each grouping of trainee(s) and trainer may operate to undertake training using the medical training computer program independently but simultaneously. It may also be possible for one trainer to utilize the medical training computer program to train multiple groups of one or more trainee simultaneously.

A trainer may utilize a computer, a tablet, a smart phone or any other device or means to provide training utilize the medical training computer program to one or more trainees. In some embodiments of the present invention, the trainer may view a video content object that is projected in the apparatus of the one or more trainees as well as additional information, such as teaching notes or other data or other video content. The trainer may also be provided with tools that allow for indicating particular segments of interest in the video content objects presented to the trainees. A skilled reader will recognize the various means of indicating particular areas of interest in the video content that may be available to the trainer.

A trainer who is closely located to the trainees, for example, such as in the same room, or other close vicinity, may provide oral instructions, lectures or other training to the trainees. The trainer may utilize the additional information provided by the medical training computer program in the course of providing oral training to the trainees.

A trainer who is located remotely from the trainees may provide oral instruction, lectures or other training to the trainees by way of an audio means, for example, such as by way of a telephone, a smart phone, a speaker system, a computer, a tablet, a laptop, video conferencing, or some other device or means of providing oral communication to a party located remotely from the speaker. In this manner, the trainees may each receive oral communication through an oral communication means, whereby the trainer may provide instruction to the trainees. A skilled reader will recognize the oral communication means and devices that may be incorporated in the present invention for this purpose, and that such means and devices may be integrated with the present invention or provided in cooperation with the present invention. For example, a trainee may use a conference telephone call simultaneously in cooperation with use of the present invention to provide oral communication, or the medical training computer program may be configured to collect the oral communication from the instructor and to distribute this to the trainees. In embodiments of the present invention, the communication between a trainer and the one or more trainees may be two-way so that the trainer can communicate orally with the trainees and the trainees can communicate orally with the trainer.

All oral communication to the trainees, whether they are closely located or remotely located from the trainer, may be provided additionally to, or simultaneously with, the presentation of video content objects to the trainees in the apparatus through the use of the medical training computer program that is linked to the video viewer element of the apparatus.

A trainer may further utilize the medical training computer program so as to present video content objects to the trainees in the apparatus, by way of the video viewer element, without providing any oral communication. For example, a trainer may present video content objects to the trainees to test the trainees' skills for use of the apparatus and/or use of the medical tool with the apparatus, or to provide for the trainee to practice such skills and use of the medical tool. A skilled reader will recognize other various instances when a trainer may not provide any oral communication to the trainees.

As noted before, medical examination of body parts with concealed anatomy usually involves use of a specialized medical examination tool, for example, such as a pneumatic otoscope in the case of pneumatic ear examinations. The proper use of such medical tools generally requires instruction and practice. If a medical tool is not used properly, the medical examination may be ineffective. For example, if a medical tool is not used properly the medical examination may be ineffective because of it results in a failure to correctly identify defects or medical conditions, or because of unnecessary discomfort, pain or injury experienced by a patient due to ineffective use of the medical examination tool.

Furthermore, the number of physical defects or medical conditions that medical professional trainees ought to be able to recognize in a patient's concealed anatomy can be significant. Prior art training methods involve displaying video content objects of defects or conditions in a book or in a slideshow. The appearance of these defects or conditions in a book or projected on a screen as part of a slideshow is different than the way these defects or medical conditions appear when viewed during a medical examination. The different appearance can be due to use of the appropriate medical examination tool, the specific lighting, the limitations for maneuvering the medical examination tool due to space restrictions defined by the relevant anatomy, or concern for the comfort of, or pain to, the subject patient. Medical professionals must be trained to recognize physical defects and medical conditions in the environment of the concealed anatomy of the body part, and as viewed through the medical tool utilized to view the concealed anatomy. Without the appropriate training or experience, medical professionals can become disoriented in conducting medical examinations of body parts including concealed geometry.

Thus, ineffective or insufficient training can contribute to medical professionals making mistakes while detecting and attempting to accurately identify the relevant physical defects or medical conditions existing in a patient's concealed anatomy. The present invention offers a means of providing the required training to cause a medical professional to efficiently and effectively accurately identify physical defects or medical conditions within concealed anatomy because it simulates the defect or condition in the anatomy and requires use of the medical tool normally utilized in a medical examination to scope and view within the concealed anatomy.

The present invention is configured to provide an effective simulation of the appearance of the body part as it would appear in the course of a medical examination or medical procedure. The present invention also is operable to permit the selection from a variety of video content objects relating to physical defects and medical conditions that may be viewed by a trainee in the apparatus simulated environment. In some embodiments of the present invention, the video content objects may be categorized into subsets for more directed use of the present invention.

The video content objects may be selected by the trainer and/or the trainee. Thus, the trainee can become familiar with viewing a wide variety of views of physical defects or medical conditions in the simulated environment and thereby become accustomed to identifying the defects and conditions as they would appear in a live subject patient. A trainee may benefit from the ability to choose particular video content objects in order to become familiar with aspects of some physical defects or conditions at his or her leisure, or to learn better how to manipulate the medical tool within the body part to view a defect or condition. For example, a trainee may choose to view specific video content objects during an individual practice session occurring outside of any trainer led session or testing session.

The wide variety of the video content objects providing examples of a range of different physical defects and medical conditions that are available for training of a trainee in the present invention, including rare defects and conditions, is an element that causes the present invention to be cost-effective over the prior art. The prior art structures and approaches do not conceive of a design or method that enables a user to access to a wide assortment of video content objects in a cost effective manner. The sheer range and volume of the video content objects available to the trainees and trainers of the present invention and the method of providing these video content objects to the trainees and trainers is cost-effective in light of the prior art and this is yet another benefit of the present invention over the prior art.

This present invention is particularly effective as a training simulation environment that provides access to an apparatus that provides training involving a significant number of different video content objects, due to the design of the medical simulation apparatus and the overall system including the computer product aspect of the present invention. The apparatus, system and computer product of the present invention are provided in a cost effective manner. In comparison to prior art systems, the training/instruction value relative to cost that is provided by the present invention is cost effective. For example, an embodiment of the present invention that is configured for the trainer to be located remotely from one or more of the trainees may permit a world-expert to train trainees that are located in areas scattered world-wide. In this manner, the present invention may permit trainees in remote areas to receive hands-on simulated environment training from world-experts. Providing this level of hands-on simulated environment training to trainees in locations remote from the world-expert, and possibly remote from other trainees, is not possible with prior art systems.

Moreover, a trainee located remotely from a training facility may utilize an apparatus, that is linked to a computer system and a trainer, or that is a relative stand alone unit, to train to recognize a wide variety of physical defects and medical conditions in a simulated environment. Such training would not be available to a remotely located trainee by prior art systems, as prior art systems offer a limited number of video content objects/video content objects to a trainee, video content objects/video content that differ from the appearance of the defect or condition in a live subject patient, and image/video content that are not viewed through a medical tool in a simulated environment of a concealed anatomy and therefore do not appear as they do to a medical professional in a medical examination. Thus, the novel and innovative design of the present invention represents a significant advancement of the art, and provides a practical and cost effective system for broader dissemination of training instructions and/or training practice to trainees.

Additionally, it may be possible for an individual trainee to utilize a stand alone apparatus for the purpose of training to use a medical tool within a body part having a concealed anatomy. When used in a stand alone manner, the apparatus of the present invention may provide video content objects to the trainee by way of the video viewer, to be viewed through the medical tool within the body part by the trainee. The video viewer may be configured to provide the video content objects for viewing without the assistance of any outside computer element. Alternatively, in another embodiment of the present invention a computer element that stores and is operable to provide the video content to a user may be incorporated in the apparatus.

In yet another embodiment of the present invention, the apparatus may be linked, by a wired or wireless means, to a computer, laptop or other device, that is local to the trainee. A version of the medical training computer program of the present invention may be installed, through a download or other means, on the local computer, laptop or other device, so that the local computer, laptop or other device is enabled to operate the medical training computer program. In this embodiment of the present invention, the medical training computer program may be configured to be operable to provide training to the trainee that may be utilized simultaneously with the apparatus, such as through oral communication teaching provided while the trainee utilized the apparatus and views particular video content objects provided to the video viewer of the apparatus by the computer program. Portions of the training may also be provided non-simultaneously with the use of the apparatus by the trainee. The computer program may further be operable to provide for practice and testing sessions whereby the trainee may utilize the apparatus to practice and test his or her skills of manipulating the medical tool within the body part and accurately identifying physical defects or medical conditions.

Furthermore, an apparatus of the present invention that is linked to a trainer, and/or a group including a trainer and other trainees, may be configured to also be utilizable in a stand-alone manner from time to time. In this embodiment of the present invention the trainee may practice or test his or her skills on the apparatus outside of any specific trainer led session or official testing session.

An additional aspect of some embodiments of the present invention that can keep the cost of the present invention relatively low is selection of components, and the arrangement of such components. The quality of the simulation provided by the apparatus and system of the present invention may remain intact even if lower cost components are selected and arranged in the present invention.

The present invention is described herein in relation to medical examinations where use of the specialized medical tools involves viewing and identification of physical defects or medical conditions. Embodiments of the present invention may also be used for training medical professional trainees to perform medical procedures that involve utilizing a specialized medical tool and interacting with medical tissue having a specific appearance. In such an embodiment of the present invention, the viewer may be operable to present to the trainee for viewing one or more video content objects showing medical tissue having specific appearances. The video content objects will cause the medical tissue to be presented to the trainee in a manner that simulates how the medical tissue would appear in connection with the relevant medical procedure, for example based on manipulations of a specialized medical tool by the trainee. The trainee may view the video content objects through the specialized medical tool that would be utilized for the medical procedure when the medical tool is within the concealed anatomy that is simulated by the physical model element of the present invention. A skilled reader will recognize that the present invention may be utilized for other training uses purposes as well.

The present invention is further disclosed herein as a training tool, however, as many physical defects, medical conditions and medical tissues affecting patients may be rarely encountered during medical practice, the present invention may also be utilized by medical professionals as a means of research, comparison or confirmation of defects, conditions or tissues viewed in live patients for the purpose of accurately identifying the patient's defect, condition or tissue. In a similar manner, the present invention could also be utilized for updating or refreshing the skills of a medical professional. For example, a medical professional who is required to examine one or more patients susceptible to defects, conditions or tissues that the medical professional has not encountered or identified in the recent past (such as defects, conditions or tissues caused by an epidemic outbreak, those prevalent in a particular population the medical professional is about to work with, or any other reason that a medical professional may need to update or refresh his or her skills) may utilize embodiments of the present invention to update or refresh his or her diagnostic skills. A medical professional about to work with a different patient population than they are accustomed to, such as children as opposed to adults, who will have different body part sizes and formations, may utilize embodiments of the present invention to update or refresh his or her tool manipulation skills. A skilled reader will recognize the variety of implementations that the present invention may have other than specifically as a training tool.

Computer System

The Figures incorporated and described herein relate to specific embodiments of the present invention. For example, the Figures relate to an apparatus and system of the present invention wherein the physical model is a body part that is an ear, or an eye. These embodiments of the present invention are provided as examples of possible embodiments of the present invention, and a skilled reader will recognize that embodiments of the present invention may incorporate physical model elements for other body parts of a human or animal having concealed anatomy, for example, such as a nose, or any other body part.

A skilled reader will further recognize that the video content objects that may presented to a user for viewing by the video viewer element of the present invention may include video content showing physical defects, medical conditions, human/animal tissue, medical tissue or any other visual content relevant to training, that pertain to any of the body parts provided as physical model elements of the present invention.

One or more physical model elements may be provided as part of embodiments of the present invention. A physical model element of embodiments of the present invention may be removable from the apparatus and system and replaceable with another physical model element. For example, a physical model element that represents a human ear may be connected to an apparatus or system of the present invention, and this ear physical model may be disconnected, or otherwise removed from the apparatus or system.

In one particular embodiment of the present invention the physical model elements consists of a physical model of a human ear that is formed such that a user may insert a pneumatic otoscope within an ear orifice, and generate a seal, as is required in connection with a real word pneumatic otoscopy examination.

In this manner, an apparatus or system of the present invention may be utilized for training involving a variety of body parts, as various physical model elements, each representing a different body part of a human or animal, may be connected to the apparatus or system.

In some embodiments of the apparatus or system of the present invention, the apparatus or system may recognize the physical model element connected to the apparatus or system at any point in time and may function to provide using the video viewer component solely video content objects relating to the body part of the animal or human represented by the physical model element connected to the apparatus or system. In other embodiments of the present invention, any of the video content objects available to the apparatus or system may be presented by the video viewer at any time.

Video Content Segmentation

The video content objects referred to in the present disclosure consist of groups of images or video frames relating to the appearance of a particular body part having concealed anatomy.

The video frames may be captured in connection with one or more manipulations involving a medical tool, where the manipulation has an impact in the appearance of the body part having concealed anatomy. A group of video frames corresponds to a particular video training session, or a session module. A group of video frames generally relates to a specific real life body part with concealed anatomy in relation which video footage has been recorded, and therefore the video attributes such as lighting, and shape/size/colour of the human/animal tissue are consistent.

For example, the application of oscillating air pressure the ear canal generates ear drum (tympanic membrane) movement of a healthy ear drum, as explained before. More specifically, the pumping of a pneumatic otoscope (when used properly) involves a range of motion that generates a particular spectrum of vacuum/pressure, and this spectrum of vacuum/pressure results in a particular range of changes in the appearance of an ear drum with particular characteristics. These changes in appearance relate to desired movements of the ear drum generated as a result of the pumping of air. A medical professional trainee must learn exactly how to use the pneumatic otoscope to generate the desired movements, and this requires a clear understanding of the actions/consequences involved, and practice using the pneumatic otoscope to produce and recognize the desired movements exactly.

One contribution of the present is an efficient mechanism to (i) capture video content related to the changes in appearance of the body part with concealed anatomy, and (ii) enable the generation of video segments of the captured video content based on input obtained from a user of a medical tool, including input related to manipulation of the medical tool by the user (where the manipulation produces changes in the appearance of the body part) in a way that the video segments are synchronized with the manipulation so as to simulate changes in appearance of the body part based in real life based on the actions of the user using the medical tool.

In one implementation of the present invention, a video pre-processing method is provided for enabling the capture of video content for use in connection with the present invention. The video pre-processing method may include: (A) trimming the video to only the motions(s) of interest (such as the motions associated with pressing of a pump of a pneumatic otoscope); (B) the trimmed video is converted to a series of video content objects or video frames (in one possible implementation there is at least one frame or for example three if movement in both directions is desired; (C) optionally the frames may be manually trimmed (for example end frames may be removed or duplicated) to show the full range of changes in appearance within the range of pressure; and (D) if required, the frames can be decimated (i.e. remove every nth frame) to reduce the number of frames.

In on aspect, a suitable number of frames may be selected for example based on data size, pressure resolution and responsiveness. For example, the inventors have found that to illustrate a pneumatic otoscopy a suitable number of frames may consist of 30-70 frames.

Figure 8A:
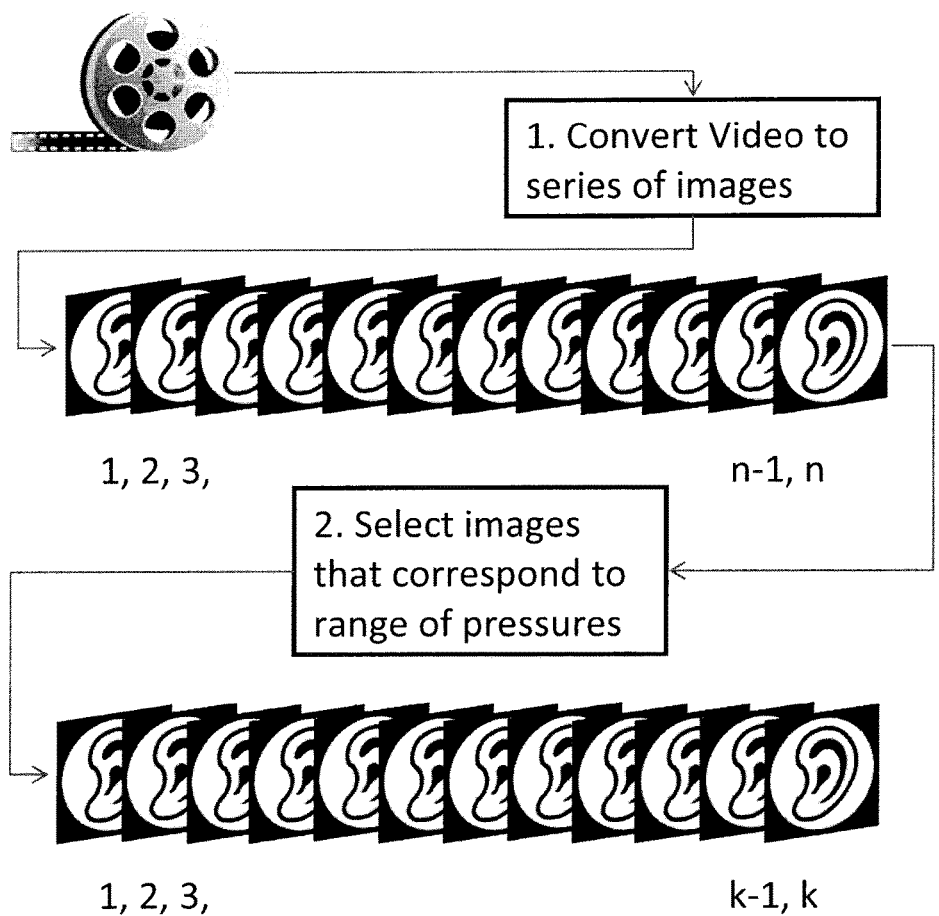
FIGS. 8a and 8b illustrate the video segmentation and indexing method of the present invention.

In another aspect of the invention, the range of pressure is defined, with a plurality of intervening values. The specific frames are they selected that relate to a particular pressure value. The specific frames are then mapped to the associate pressure values. For example, the frames may be encoded with a value that is associated with the pressure value, as shown in FIG. 8a. For example, a frame index may include a series of frame identifiers and associated pressure values.

Figure 3:
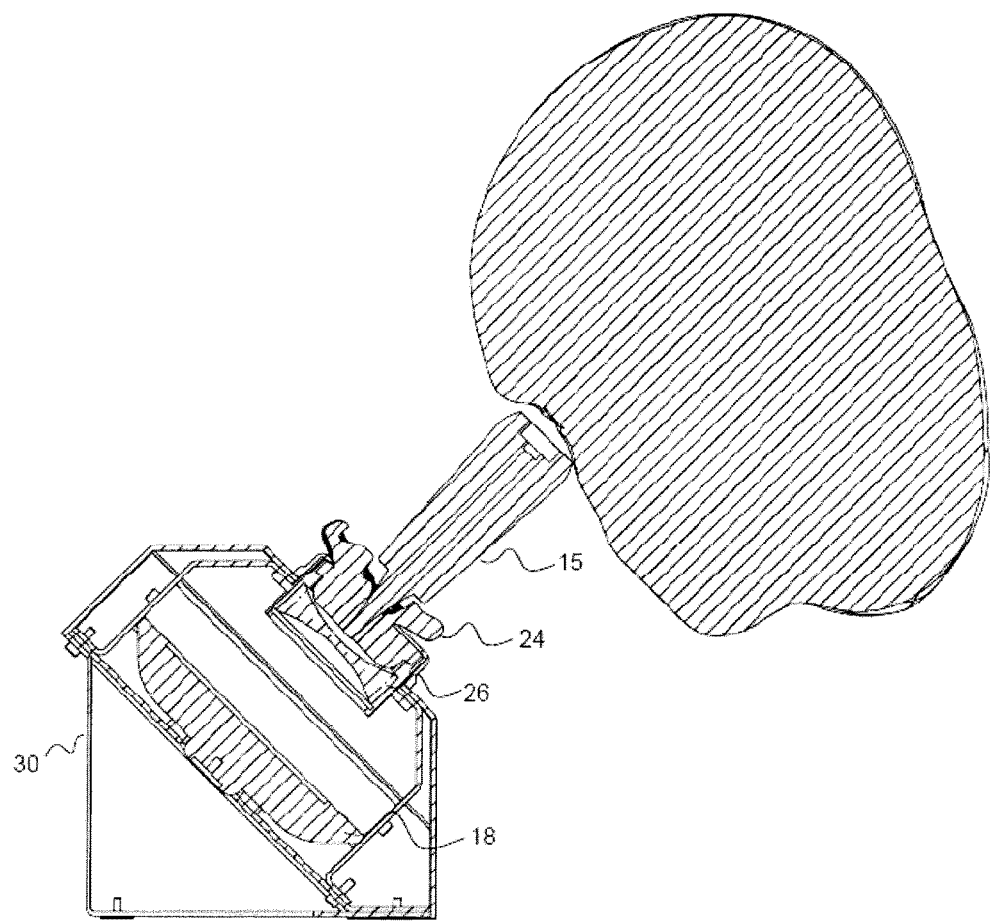
FIG. 3 is a sectional side view of a representative embodiment of the medical training simulation apparatus of the present invention.

As further explained below, in one embodiment of the present invention, the apparatus of the present invention includes a pressure sensor. This pressure sensor may be integrated with the main apparatus (as shown in FIG. 3) or may be implemented as a separate component, as shown in FIG. 1b.

Figure 8B:
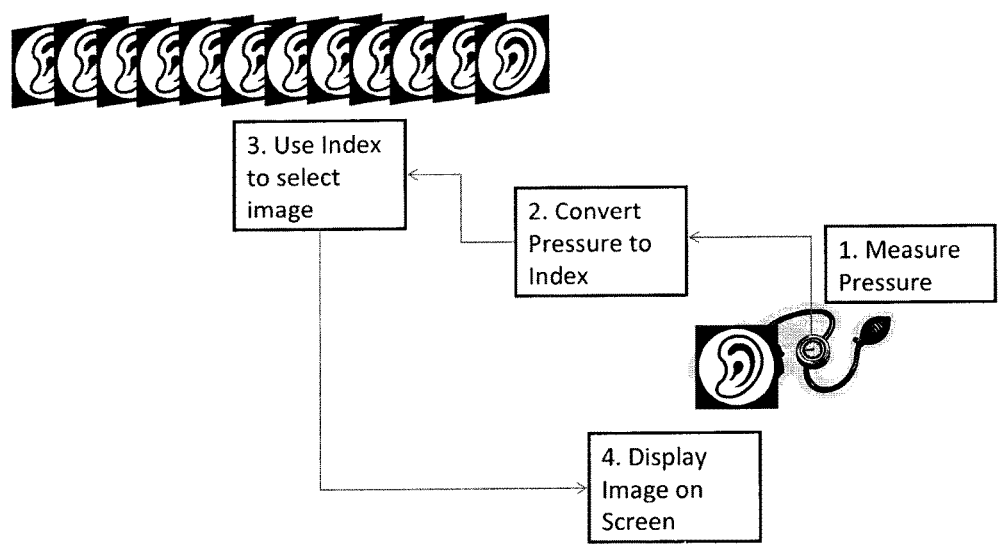

In another aspect of the present invention, the method of the present invention includes:

(A) a user or a computer provides a training session ID, the computer access the associated video frames and the applicable frame index;

(B) The user inserts a pneumatic otoscope into the apparatus, and creates (or may attempt to create) a seal;

(C) The user depresses the pressure bulb, thereby generating airflow that creates vacuum/pressure; and (D) the pressure sensor generates a pressure value number, and provides this to the computer; the computer accesses the frame index, and retrieves the appropriate image and displays the appropriate image in the video viewer, as shown in FIG. 8b.

This process is repeated dynamically in response to the series of pressure values generated as the user actuates the pressure bulb. As a result a series of frames from the video content are displayed in a manner that is consistent with the particular pressure applied by the user using the medical tool. A skilled reader will appreciate that by selecting appropriate computing and image processing resources, smooth matching of the display of video frames corresponding to the real time manipulation by the user of the pneumatic otoscope is achieved.

The choice as to which video training session or module is accessed may be made by the trainee, the trainer, or the computer program element of the present invention, depending on the embodiment of the present invention and the mode of operation of the present invention.

For example, in a mode whereby a trainee may test their skills, the computer program element of the present invention may choose the video content objects presented by the viewer, whereas, during a training session involving a trainer, the trainer may choose the video content objects by selecting the video training session or module to be accessed and displayed.

A skilled reader will recognize all of the possible means of providing the video content objects and associated methods of operation may be incorporated in embodiments of the present invention.

A skilled reader will understand that video segmentation technique explained above may be applied to other body parts.

System Implementation

In one aspect of the invention, the video content segmentation technique explained above is integrated with a medical training system of the present invention that incorporates at least one medical training simulation apparatus (may be referred to as the "base system" in the present disclosure). A representative embodiment is shown for example in FIG. 1b.

FIG. 1a shows a representative implementation of the computer system of the present invention for pneumatic otoscopy.

The present invention, as applied to pneumatic otoscopy may enable:

(A) trainees to learn the correct amount of pressure to be applied to perform the examination correctly (little pressure is actually required in order to conduct the examination);

(B) trainees to learn how to seal the ear correctly, otherwise trainees will assume incorrectly that there is fluid in the middle ear; and (C) trainees learn to recognize different parameters that may affect movement/appearance of the inside of the ear (for example if a patient has had ear infections this may affect the relative movement of the ear drum);

The medical training computer program of the present invention may include a graphical user interface that displays for example one or more ranges. For example the medical training computer program of the present invention may show a "green" pressure range that may constitute a target range based on examination efficacy and patient comfort. This aspect of the invention may direct the trainee to learn to apply the requisite vacuum/pressure to stay within this range.

Various different implementations are possible, for example:

(A) different pressure sensors may be used for the pneumatic otoscopy implementation; and (B) numerous different components or technologies may be used to sense the direction of the opthalmoscope (for example in one implementation an adapted opthalmoscope may include position sensing components—such as accelerometers and magnetometers—and associated programming for example in its handle, in another implementation a motion/position detection apparatus is adjacent to the opthalmoscope and is configured to track the movement/position of the opthalmoscope).

The computer system of this embodiment of the present invention may include at least one computer 10. The computer may be a desktop computer or laptop that is linked to a mouse 28, screen 30 and keyboard 27. A trainer 32 may be able to operate the computer by way of the mouse, screen and/or keyboard. It should be understood that in other embodiments of the present invention, the computer may also be a tablet computer or any other computer device operable to allow a trainer access to the functions of the medical training computer program of the present invention. In particular, the trainer may operate the computer to view the video content objects of physical defects or medical conditions that are simultaneously displayed to the one or more trainees by operation of the at least one medical training simulation apparatus.

During a training session that is led by a trainer, the trainer must be able to view the video content objects that are simultaneously provided to each trainee in the trainer's group by the viewer of the apparatus because the trainer will explain the various features of the physical defects or medical conditions shown in the video content objects to the trainee. The trainer may thereby provide information to the trainees regarding the defects or conditions that a trainee needs to know in order to be able to recognize and become familiar with the defects and conditions. The computer operated by the trainer may further be operable to provide tools to the trainer whereby the trainer can point to or otherwise highlight notable aspects of the defects or conditions shown in the video content objects to the trainees.

The computer program of the present invention may further be operable so that the computer may be used by the trainer user to initiate, follow and/or control one or more medical training routines embodied in the medical training computer program of the present invention.

As shown in FIG. 1a, the computer 10 may be linked, for example, such as through splitter 14, to a plurality of medical training simulation apparatuses 12, each being a simulation unit. The computer may incorporate or otherwise be connected or linked to a plurality of video content objects 16. The video content objects may include archived video content objects. The video content objects may be stored in a database. The plurality of video content objects 16 may include video content objects showing physical defects, medical conditions or medical tissues pertaining to a specific body part.

The plurality of video content objects may be displayed to a trainee in a medical training simulation apparatus by way of operation of a video display 18 that is a viewer element of the apparatus whereby video content objects are presented to a trainee as a viewable image. The plurality of video content objects that may be displayed in each medical training simulation apparatus may include a wide range of video content objects showing a number of different physical defects, medical conditions or medical tissues. For example, the video content objects may include video frames of physical defects or medical conditions that are relatively rare, and that therefore may not be found in human or animal subjects that may be available for medical training purposes. In this way, by operation of the present invention, one or more trainees may access, at a relatively low cost, a complete or substantially complete set of video content objects, meaning that the set of video content objects covers a wide variety of possible physical defects or medical conditions, and potentially all known defects and conditions, that can affect a particular body part.

It is also possible for the video content objects to be stored as identified as being groupable into subsets, or for subsets to be provided as image sets. For example, a subset may include video content objects relating to physical defects, medical conditions and/or medical tissues that are prevalent in a particular area or for a particular segment or group of a population. As another example, a subset may include video content objects relating specifically to rare defects, conditions or tissues. As yet another example, a subset may include video content objects relating defects, conditions or tissues encountered specifically in populations of a particular age, such as children or aging adults. In this manner, embodiments of the present invention may provide sets or subsets of video content objects, and for the purpose of training medical professionals, research or refreshers for medical professionals, or confirmation of an encounter with a rare defect, condition or tissue by a medical professional. A trainee or medical professional may not require exposure to a wide variety of video content objects in some instances of use of the present invention, and embodiments of the present invention may be operable so that a trainee, trainer or medical professional may choose to limit use of the present invention to a subset of video content objects.

The medical training simulation apparatus 12 includes a video display 18 and may include a controller 20 that provides on board control of the video display 18, whereby one or more video content objects selected to be consecutively displayed to the trainee utilizing the apparatus by way of the video display. It should be understood that the control function of controller may be provided by connecting the apparatus 12 to the computer 10. This connection may be by way of a wired or wireless means, for example, such as a USB, a wireless data connection or any other suitable data connection between the apparatus and the computer. Through this connection, the computer program of the present invention that is operable by the computer is also operable to control the video content objects displayed to the trainee by way of the video display.

By including the controller in the simulation unit, however, the simulation unit may enable one or more simulations by operation of the simulation unit as a self-contained, or stand alone, unit. This may enable the medical training simulation apparatus to be used in connection with a training routine initiated or directed by a trainer user of the computer, or a practice routine initiated by a trainee user of the computer without the involvement of the trainer user.

The simulation unit 12 may also include an optical means 22 that may be optics operable to alter the one or more video content objects displayed by the video display 18. This alteration of the image by the optical means may be configured to cause the appearance of the one or more video content objects to be a realistic appearance that is relative to the manner in which the defects or medical conditions would appear, using a medical examination tool, in a medical examination of a real subject patient.

A physical model may be incorporated in the simulation unit, or mounted on the simulation unit. The physical model may be formed to simulate the geometry that the medical professional is required to navigate using the medical examination tool when conducting a medical examination simulated. The simulation geometry may differ for particular embodiments of the invention, and the physical model may represent different body parts of a human or animal that has concealed anatomy.

A skilled reader will further recognize that the physical model of embodiments of the present invention may be formed to represent other body parts and to simulate the concealed geometry of such other body parts. Moreover, a skilled reader will recognize that multiple physical models may be attachable to the housing of the apparatus, so that multiple physical models, representing a variety of body parts, may each be individually connected to housing of the apparatus, so that one physical model is connected to the apparatus housing at one time. Multiple physical models may thereby be utilized with the other elements of the apparatus, including the video display, so that the apparatus and system of the present invention may provide a means of training in relation to a variety of body parts. The computer, video display and/or the optical means may be configured to cause the video content objects displayed on the video display to simulate the appearance of defects or conditions shown in the video content objects in the apparatus to appear as such defects or conditions appear in a live subject patient. The present invention may therefore provide a means of simulating the use of medical tools relevant to several body parts (for which there are physical models provided with the present invention) to view a simulation of the environment of a variety of defects and conditions viewable through the use of the medical tool.

As shown in FIG. 1b, a trainee 34 may utilize a medical tool 15, for example, such as pneumatic otoscope. The medical tool may be inserted within the physical model by the trainee. The trainee may therefore utilize the medical tool inserted within the physical model to view an image presented through the video display by way of optics. The optics and video display may be incorporated in the apparatus, and the physical model may be attachable to the apparatus.

In an embodiment of the present invention, a memory (not shown) may also be incorporated or connected to the of the simulation unit and linked to the controller such that the video content objects may be integrated with the simulation unit.

In another embodiment of the present invention, an input means (not shown) may be linked to the controller, such that a trainee user of the simulation unit may selectively control the simulation unit to vary the video content objects displayed by the video display. Any manner of input means may be used such as a computer device linked to the simulation unit (not shown) for use by the one or more trainee users. The input device is operable so that the trainee user may select one or more libraries, sets or subsets of video content objects stored to the database. The input means may be integrated with the simulation unit, for example, such as by providing access to a trainee to an external touch screen or pad for interfacing with one or more computer program components for displaying information. Access may further be provided by way of one or more menus whereby one or more libraries, sets or subsets of video content objects may be selected by the trainee, and a trainee may navigate within each selected library, set or subset of video content objects.

The computer program of the present invention may be implemented on the trainer side computer or a trainee side computer. The computer program may generally be configured so as to enable the creation of a training routine. The training routine may be developed and designed to provide training relating to and involving the display of one or more video content objects of physical defects or medical conditions. For example, the computer program may include or be linked to a software utility for creating a trainer lesson or presentation. The trainer lesson or presentation may include one or more video content objects, and also associated text, links, audio files, animations, or other content that serves the purpose of instruction or training in connection with the video content objects. The content may be used by a trainer to explain the features of the video content objects or associated information such as medical information concerning the defects or medical conditions shown in the video content objects.

As discussed herein, the training session may involve an audio component and oral communication means or device, whereby oral communication between the trainee(s) and a trainer may occur to facilitate a lesson. The audio communication means or device may be integrated with the present invention system or may be distinct from the system, but cooperative with the system (such as a separate dial-in telephone conference call linking the trainer and the trainee(s), or a video conference on a laptop, or an online streaming video session on a computer, etc.). The communication means or device may include a telephone, a smart phone, a tablet, a computer, a laptop, a sound system or speaker system, or any other communication means or device. The oral communication may be bi-directional between the trainee(s) and trainer, or may only flow from the trainer to the trainees.

The computer program may further provide automated training sessions to one or more trainees, whereby no trainer is involved in the training session. Training sessions may involve the apparatus as well as segments whereby the trainee(s) views information, videos, or other content on a computer screen and does not utilize the apparatus, or may be provided solely through use of the apparatus. The automated training sessions may include an audio component which may be provided by a communication means or device that is any communication means or device described herein, and is a communication means or device integrated, linked to or otherwise connected with the present invention.

The lesson or presentation, by operation of the computer program, may be controlled by a trainer or an automated training session of the computer program, may be linked to the display of the video content objects in the one or more apparatus. In this manner the trainer (or the computer program) navigates within the lesson or presentation and the medical training apparatus automatically displays the image or designated video content objects indicated by the computer program, or otherwise chosen by the trainee. For example, the lesson or presentation operated by the computer program may include a slide or equivalent with information and that is linked to at least one of the video content objects. The video content objects for the lesson or presentation will be shown in a consecutive manner to the trainee through the video display of the apparatus, in accordance with the progression of the lesson or presentation.

The computer program of the present invention on the trainer side may be operable to display for the instructor a user interface including one or more areas. Each area may show to the trainer the image that the trainee sees in the apparatus in real time or near real time. A trainer is thereby able to conduct a training session for one or more trainees and in real time or near real time, wherein he or she may deliver instructions in response to what the trainer sees which includes the image that the trainee is viewing in the apparatus. The trainer may additionally see any or all of the following: further information; step-by-step instruction; detailed direction; feedback; or any other information relating to the lesson or presentation.

An advantage of the present invention over the prior art is that the trainer can provide effective instruction to more than one trainee student at a time and can be fully aware of the image that is viewable by each trainee as the trainee is viewing said image. Prior art technologies generally merely provide for one-on-one training sessions and the trainer is not necessarily aware of what the student is viewing at any particular point in time.

In another aspect of the instruction control computer program, the program includes a lesson plan creation component that provides instructions with a series of tools or templates for creating or assembling, and then storing to a database, a new lesson plan, tutorial or other training module, for use in connection with the system described. The lesson plan creation component of the present invention allows for the creation of different lesson plans based, for example, on the specific subject of one or more medical video content objects. As an example, in connection with an otoscopy implementation of the present invention, different lesson plans may be created depending on the subject patient age, given that there are differences in the parameters of otoscopy that are driven by age. In such a training module, a first lesson plan may relate to otoscopy on an infant, a second lesson plan may relate to otoscopy for a juvenile, a third lesson plan may relate to otoscopy for an adult. A skilled reader will recognize the wide variety of lesson plans and modules that may be created an incorporated in the present invention.

In some embodiments of the present invention, one or more resources associated with the computer, or resources linked to or otherwise connected with the computer, may be implemented in a web server architecture or using cloud resources. This may enable central access to shared resources including medical video content objects or lesson plans. Access to medical video content objects or lesson plans may be provided as a web service or cloud service whether based on a subscription basis, pay per use basis or other model. Such access may also assist trainees having an apparatus of the present invention who are located remote areas to receive training that would not otherwise be available in such remote locations.

Embodiments of the present invention may also integrate one or more sensors or cameras operable to collect data regarding the trainee's actions. The collected data may be analyzed by operation of an assessment module of the computer program to generate assessments of performance, either automatically or on a user guide or approved basis. For example, the collected data may indicate force of a medical tool upon the physical model, depth of insertion of a medical tool into concealed anatomy of the physical model, time lapsed during use of a medical tool to view a simulated physical defect or medical condition shown as an image in the apparatus, or any other data relating to the use of the apparatus by a trainee. The analysis may provide feedback to a trainee such as whether aspects of the manipulation of the tool would be likely to cause pain for a patient, whether the length of time to view the defect or condition would likely cause discomfort for a patient, or any other analysis results.

In some embodiments of the present invention, and for some purposes, for example, such as a review or a practice session, the display of the video content objects may be controlled by the trainee. If the trainer is involved in the session or linked in to the session, for example, such as review of a scheduled practice session, the computer program may display a screen to the trainer that shows the image being viewed by the trainee that was selected by the trainee.

If multiple trainees are individually controlling the display of video content objects, for example, such as multiple trainees in a group of a trainer and trainees, the trainer may be able to view each of the video content objects being viewed by each of the trainees as the video content objects are viewed by the trainees simultaneously, or to choose to see the video content objects being viewed by individual trainees or a sub-group of trainees. In such an embodiment of the present invention, the computer may be connected to two or more medical training simulation apparatuses. The computer program may be operable to display multiple screens to the trainer, each screen displaying the image then selected by the trainee for viewing by operation of the medical training simulation apparatus. The trainees in this case may control the display of video content objects, whether based on, for example, a sequence defined by a lesson plan, or based on their individual discretion. If a trainee has a question, or the trainer wishes to selectively provide instruction to one or more trainees, the trainer may select the medical training simulation apparatuses of interest from the multiple screens (for example, such as is identified by a label associated with the particular apparatus or its user), to see what is being viewed by the trainees, and provide comments, instruction or feedback accordingly to one, several or all of the trainees.

In one embodiment of the present invention, the lesson or presentation of video content objects may automatically follow the video content objects viewed by one or more users simultaneously as controlled on the trainee side.

In an embodiment of the present invention, the trainer side computer program may be configured to be responsive to input from the trainer user (by way of the computer) regarding navigation between the video content objects, slides presented to the trainer that incorporate information only displayed to the trainer and one or more video content objects, or other similar content. The trainer side computer program may be operationally linked to the one or more medical training simulation apparatus, so that the computer program controls the video display and causes it to display the image selected by the trainer by way of the trainer's navigation between the video content objects, slides or other similar content.

In an embodiment of the present invention wherein a computer is linked to the medical training simulation apparatus at the trainee side, the computer may be configured to display the lesson or presentation, or a trainee version thereof. This may be useful to check features highlighted in the version of the video frames shown in the medical training simulation apparatus, or to view associated information displayed in the lesson or presentation such as magnified features of specific area, links to associated information, and other content.

In another embodiment of the present invention, the trainer side computer program may be operable to allow the trainer to initiate the computer program to mark the video content objects, for example, such as marking using a digital overlay. Such marking may be utilized to highlight, lasso, point to or otherwise select one or more areas of the one or more video content objects. A suitable input means, for example, such as a digital pen or mouse, may be utilized for marking. The trainer may further initiate the video display in the apparatus of each trainee connected to the trainer to show these aspects marked in the video content objects, as initiated by the trainer. So that the one or more video content objects displayed by the video display of each apparatus utilized by a trainee, will show the image with the markings incorporated in the image by the trainer.

Alternatively, markings on one or more video content objects may be displayed by the computer on the trainee side. As a still other alternative, the trainee side computer program may enable the same or similar operations which may serve to highlight the areas of one or more video content objects. For example, one or more trainees may be able to highlight a specific area in a video frame. The trainees may utilize this facility of the present invention to mark a section of a video frame that the trainee has a question about so a trainer can better understand the trainee's question. This facility of the present invention may have other uses as well.

Embodiments of the present invention may be implemented to achieve distance learning. One or more features described above may be used to enable training where the trainer and one or more trainees are at different locations. Each trainee will have an apparatus to use during training session and may also have a trainee side computer, although a trainee side computer is not necessary for remote training. The trainer will have a trainer side computer operable to run the training computer program. It will be obvious to a person skilled in the art that a suitable remote access and control technology can be deployed between the computer and one or more medical training simulation apparatuses at one or more remote locations from the computer, and also optionally between the computer and the trainee side computer associated with the medical training simulation apparatus at the trainee location, so as to enable remote training operations. For example, the computer may be linked to one or more medical training simulation apparatuses to enable remote control of each apparatus by the trainer by operation of the trainer's trainer side computer program.

In embodiments of the present invention, the database may be linked to a web server or cloud computing network, optionally configured to enable upload and sharing of video content objects by multiple users in multiple locations. The database linked to a web server or cloud computing network may further be operable to download of one or more video content objects from a plurality of medical training simulation apparatuses linked to the web server or cloud computing network via the Internet.

The system of the present invention may also incorporate a testing component that requires, for example, each trainee to follow an exercise that involves viewing of one or more the video content objects of specific physical defects or medical conditions using the medical training simulation apparatus. The user may be required to provide feedback, for example, such as orally answering a question so that the answer is captured using a voice recording, providing input to a computer linked to the apparatus, or engaging an input means integrated with the apparatus. Questions in a test session may be for example, multiple choice questions associated with the image and displayed by the computer, and/or may ask a trainee to identify the defect or condition shown in a particular image.

The answers provided by the one or more trainees in a test session may be captured, and then analyzed for accuracy. In a particular implementation of the present invention, the results may be analyzed, and tracked over multiple training sessions and/or test sessions so as to monitor progress of training and report on the same. The results for each trainee may be displayed to the trainer, said trainee, and/or all trainees. Displaying results of all trainees for all of the trainees to see may foster competition amongst the trainees. Results may further be analyzed relating to a group of trainees, or all trainees utilizing the system.

Other aspects of gaming may be introduced in the present invention, for example, such as by defining rules requiring the trainees to identify correctly a particular number of physical defects or medical conditions from a series of video content objects correctly, without exerting force using their medical examination tool that exceeds a defined threshold for a selected area of the physical model. Force exerted may be calculated using a sensor, for example, such as a sensor array integrated with the physical model. In this manner, both identification of defects and conditions as well as skilful manipulation of the medical tool in the body part may be taught and assessed by the present invention. A skilled reader will recognize how other sensors may further be integrated in the physical model to provide for other types of training and assessment of the diagnostic and medical tool manipulation skills of the trainees.

A skilled reader will recognize that numerous training sessions, routines and operations are possible in accordance with the present invention. Embodiments of the present invention may incorporate various system and network configurations to facilitate and support particular training sessions, routines and operations, and to provide a wide range of possible medical training options and parameters. A skilled reader will recognize that various configurations and derivatives may be incorporated in embodiments of the present invention.

Structure of Medical Training Simulation Apparatus

FIGS. 2-6 illustrate a particular embodiment of the medical training simulation apparatus of the present invention that is configured to be utilizable for otoscopy training. In one particular embodiment of the present invention, as shown in FIG. 1b:

(A) the main apparatus is designed for otoscopy training;

(B) the physical model and associated lens may be removed and replaced with another physical model lens, such that the system of the present invention is interchangeable between different applications;

(C) the physical model shown in FIG. 1b is configured for pneumatic otoscopy and therefore has an ear model that is suitable for creation of a seal, and also the physical model includes an opening that receives a hose, and the hose is connected to a pressure sensing module (connections are sealed to ensure accurate pressure sensing).

One aspect of the design is that the apparatus may easily be reconfigured for different simulation applications, while maintaining the ease of manufacture and affordability of the system.

Figure 7A:
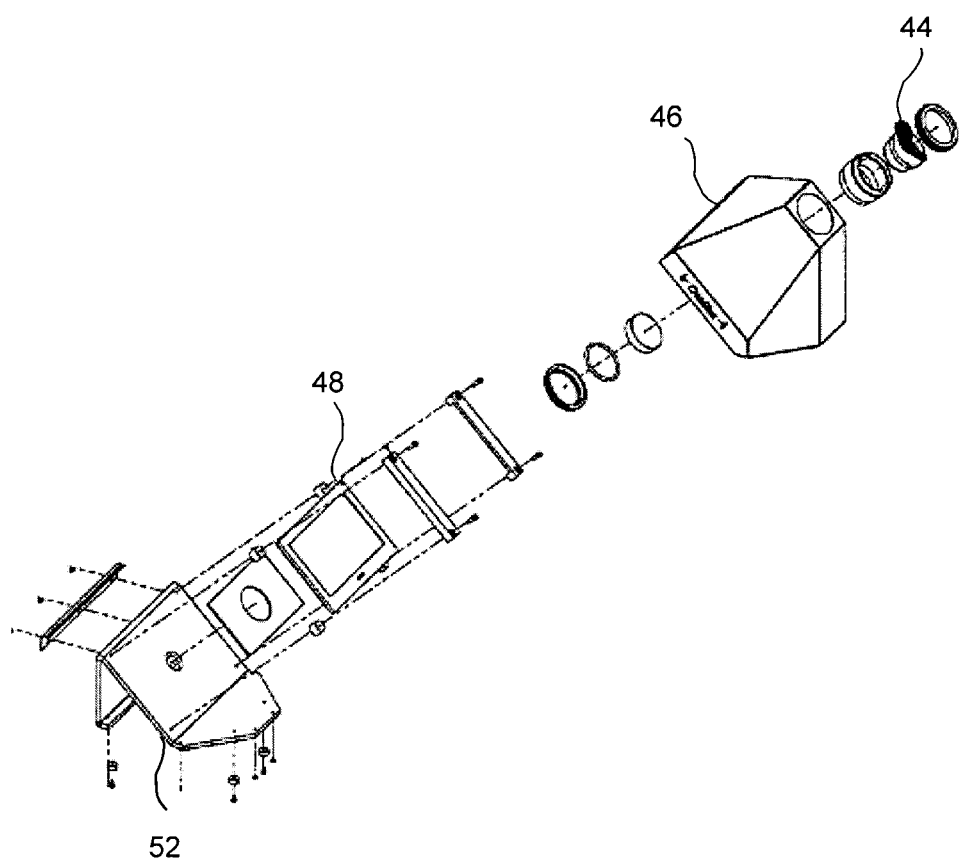
FIGS. 7a to 7f illustrate particular embodiments of a base for the apparatus of the present invention.

FIG. 7a shows one possible implementation for use in pneumatic otoscopy training.

FIGS. 7b to 7f show different design aspects of a possible embodiment of the main apparatus.

FIGS. 8a and 8b illustrate the video segmentation and indexing technique of the present invention.

Figure 2:
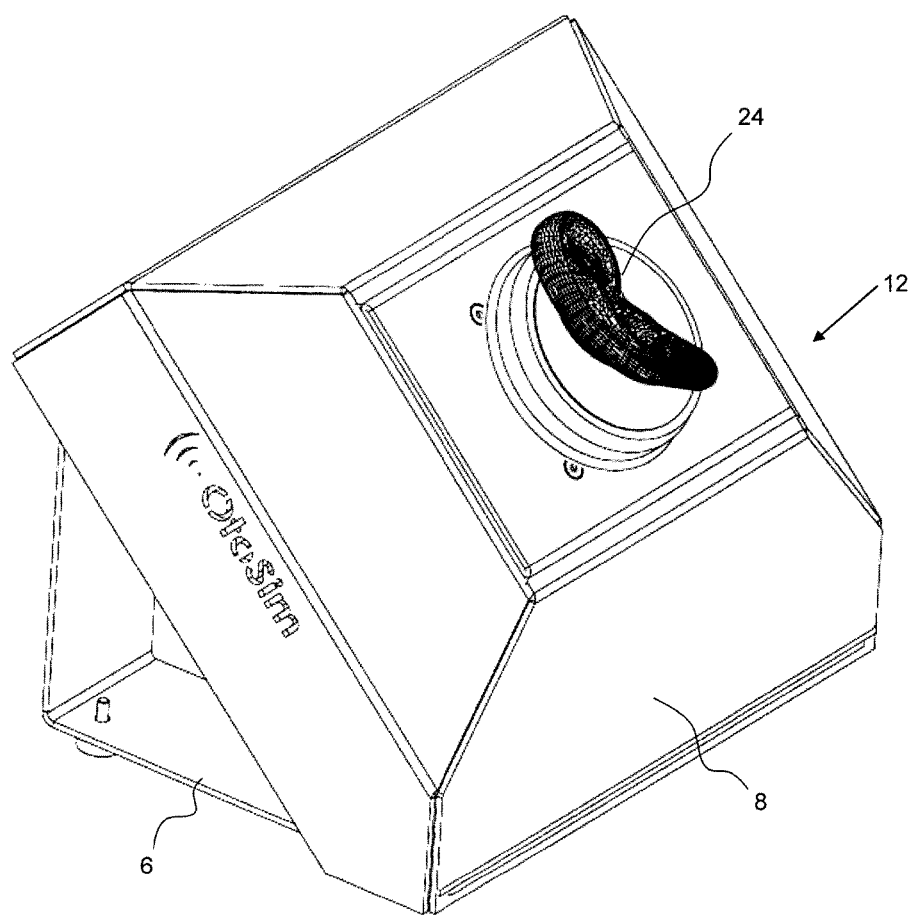
FIG. 2 is a perspective view of a representative embodiment of the medical training simulation apparatus of the present invention, showing the exterior of the apparatus.

Now referring to FIG. 2, the medical training simulation apparatus 12 may incorporate a housing that comprises a base 6 and a top portion 8. The physical model 24, for example, such as is a representation of a relevant body part including concealed anatomy, and that is an ear in the specific embodiment shown in FIG. 2, is attachable to said housing, and specifically to the top portion of the housing. When the housing is attached to the physical model, the combined elements define a physical structure that enables the simulations and the training described herein.

The top portion includes a physical model, or a portion of the physical model. The physical model is used as part of the simulation of the medical examination or procedure involving the particular body part represented by the physical model. The base portion enables the unit to rest upon a surface in a manner that is flat, of virtually flat. For example, the base portion may rest upon a table. The base portion may be formed to hold and support the apparatus in a stationary position.

FIGS. 2-6 and 7a-7f illustrate particular embodiments of the invention, configured to assist in training for otoscopy and, therefore, the apparatus includes a physical model representing an ear model or simulated ear. The physical model may be disposed around the top of the medical training simulation apparatus. The physical model may be formed using a suitable material to simulate the body part, including its physiology, such as flexibility. For example, the physical model may be formed of a material that is easy to clean and is flexible to simulate the pulling of the body part. In embodiments of the present invention wherein a physical mode represents an ear, the physical model may be flexible to simulate pulling of the ear in order to displace the ear canal to permit viewing of the inside of the ear using the otoscope. A skilled reader will recognize that other physical models representing other body parts having concealed anatomy may be attachable to the top portion of the apparatus, and that suitable materials may be used to form such physical models to simulate characteristics of the body parts.

As an example, the physical mode that is representative of an ear, in one embodiment of the present invention, may define an opening and concealed anatomy, similar to the shape and appearance of the opening and concealed anatomy of an ear of a subject patient, being a human or an animal. The opening and concealed anatomy of the physical model representing an ear may extend to define a portion that simulates the ear canal, or the opening of the ear model may communicate with a channel defined by the physical structure of the medical training simulation apparatus, thereby simulating the ear channel.

The appropriate medical tool, as would be used in a medical examination of the body part represented by the physical model, may be inserted within the physical model. For example, a pneumatic otoscope 15 may be inserted within the physical model 24 representing an ear, as shown in FIG. 3. The physical model 24 may be attached to the top portion of the housing of the apparatus. A support frame 30 may support the apparatus upon a surface.

In an embodiment of the present invention, the physical model that represents an ear may be configured such that the outside of the ear of the physical model (which corresponding to the outside portion of an ear) may be pulled by the medical practitioner trainee to cause the ear canal of the physical model to become straightened to thereby permit the insertion of the otoscope (being the medical examination tool appropriate to be used with this particular embodiment of the present invention). In one embodiment of the present invention, the ear model may be formed from silicone.

The location and position of the physical model that is an ear upon and incorporated with the apparatus may be such that the portion simulating the ear canal is disposed such that a trainee is able to insert the otoscope through the opening of the physical model of the ear into the simulated ear canal of the physical model. In embodiments of the present invention, the ear canal portion of the physical model may be sized substantially to conform to the average size of a human or animal ear canal, so as to enable full insertion of the tip of an otoscope, similar to how an otoscope would be used on a human or animal subject. In another embodiment of the present invention, the ear canal portion may be configured to represent an ear having a known condition, for example, such as the ear canal portion may be an angulated ear canal portion or an ear canal portion with meatal stenosis (a narrowing of the ear canal) so as to add complexity to the simulation parameters. In another embodiment of the present invention, the physical model representing an ear may be configured to be reflective of pediatric conditions with an ear canal diameter ranging from three to 10 millimeters in diameter. A skilled reader will recognize how physical models representing other body parts may also be formed to simulate use of an appropriate medical tool and known conditions that may affect the body party represented by the physical model.

As shown in FIG. 3, the video display 18 may be disposed within the medical training simulation apparatus, and aligned with the physical model 24 such that the video display 18, or more specifically an area of the video display 18, is visible through the opening of the physical model 12. For example, if a physical model that represents an ear is attached to the apparatus, when the trainee user pulls the exterior ear portion of the physical model the video display is visible through the simulated ear canal. In a one implementation of the present invention, the apparatus may be configured such that the video content objects are displayed on the video display so as to generally confirm with said area.

It should also be understood that the physical structure of the medical training simulation apparatus, in embodiments of the present invention, may be arranged and configured such that the physical model of the body part is spaced apart from the video display. This configuration may be applied in part to simulate the distance between aspects of the concealed anatomy that the trainee seeks to view during the simulated medical examination using the medical examination tool. The particular anatomy of the body parts with concealed geometry tends to be at a defined distance from the reach of the medical examination tool. For example, in the case of otoscopy, the defects or medical conditions of interest tend to be further along the ear canal than the otoscope can reach. This affects the appearance of the physical defects or medical conditions as such defects or conditions are viewable by a medical practitioner looking within the ear of an applicable subject patient. In some cases, otoscopy involves illuminating parts of the anatomy distal to the end of the otoscope. The present invention may be configured to display the one or more video content objects in a way that simulates how the physical defects or medical conditions would appear in a live subject having the same defects or conditions.

The present invention may be defined in accordance with a configuration for a medical training simulation apparatus that achieves the objective of providing a realistic simulation representing how physical defects or medical conditions may appear in a live subject patient, but that also uses an arrangement of elements that is inexpensive to produce and easy to use.

The video display of embodiments of the present invention may be a standard digital display unit, for example, such as an LCD. This enables the use of a relatively low cost image display means, for example, such as a standard, off-the-shelf LCD video display that is common enough to be at a low cost due to economies of scale. As a further example, the LCD screen may be a 7 inch USB monitor that displays video content objects of various pathologic conditions.

The fact that the medical training simulation apparatus of the present invention is configured in a way that it enables the use of this type of a display unit contributes to the relatively low cost of the apparatus of the present invention. This in turn makes the apparatus accessible to a significant number of medical practitioners. Some prior art systems require expensive equipment, which some practitioners cannot afford prior art systems are prohibitive so that some practitioners cannot access or use such prior art systems. Accessibility aspects provided by the apparatus of the present invention therefore offers access to improved training for medical practitioners in medical examinations involving body parts with concealed geometry generally.

In embodiments of the present invention, the video display may be connected to a USB port presented externally by the physical structure of the medical training simulation apparatus. The USB port may permit, for example, a cable connection to the trainer's computer. The USB port may alternately also permit a connection to a computer associated with the trainee. The USB port may further permit a connection to each of the trainer's computer and a computer associated with the trainee.

In one implementation of the present invention the medical training simulation apparatus unit may be configured such that the one or more video content objects displayed by the image display unit are sized so that, when viewed from the opening of the physical model, the one or more video content objects covers all of the area visible through the opening of the physical model. In one embodiment of the present invention, the image projected on the surface of the video display (e.g. standing image or video projection) may range in actual size, for example, such as from 2 to 4 inches in diameter. Image size may be modified depending on the nature of the image and the various optical parameters of the simulation apparatus.

The one or more video content objects and/or their display by the video display may be adjusted such that the physical defects or medical conditions may be viewed using the appropriate medical examination tool. For example, the average otoscope magnifies at around 3× or 4×. The one or more video content objects may be displayed such that when viewed using an otoscope (with the relevant magnification) they will appear as they would when viewed in a live human or animal subject patient during a medical examination or procedure.

The one or more video content objects themselves may be made or selected so that they have an appearance, using lighting, exposure and other photographic techniques, that is consistent with the appearance of the relevant physical defects or medical conditions of the applicable body parts represented by the physical model attached to the apparatus.

The contour of the one or more video content objects may be made to correspond to the profile of the opening defined by the physical model.

In another embodiment of the present invention, the one or more video content objects may be displayed by the video display unit as relatively high resolution video content objects. The tissue viewed inside in the body part during the course of the medical examination or medical procedure will generally not appear using the medical examination tool as a high resolution image, but rather will be visible to the medical practitioner using the medical examination tool in a way that exhibits a lower resolution or grainier quality. This is so because: (a) the tissue is spaced apart from the point of insertion of the medical examination tool; and (b) the appearance of the tissue is also affected by the magnification and illumination that is possible using the medical examination tool. It is therefore desirable in embodiments of the present invention to display the accurate colour and physical characteristics available using the relatively high resolution video content objects, but the video content objects may be modified in some way to simulate how these features would present in a real medical examination of a live subject patient.

In yet another embodiment of the present invention, the video display may be used and arranged to align with an optical means so as to provide a simple and cost effective means for altering the way in which the video content objects appear to the human eye using a medical examination tool in relation to body parts with concealed geometry, while maintaining the colour and physical features of the video content objects of the medical defects or conditions.

To this end, as shown for example in FIG. 3, the medical training simulation apparatus may be arranged in away that it permits the physical structure to retain an optical means, for example, such as a lens 26. The lens may be held in place, disposed between the channel porion of the physical model and the video display 18. The lens may be operable to, in effect, de-pixelate the one or more video content objects. The lens may be selected to provide an effective means to simulate the appearance of the physical defects or medical conditions shown in the one or more video content objects.

In one embodiment of the present invention, the lens may be selected such that in combination with, for example, the magnification of the medical examination tool (e.g. the 3× or 4× magnification provided by a standard otoscope), the lens provides sufficient de-pixelation of the one or more video content objects. This may simulate the appearance of the physical defects or medical conditions shown in the video content objects as they would appear in a medical examination of the human or animal subject patient, in accordance with the image that applicable subject of the image (e.g., human or animal). In one embodiment of the present invention, the selected lens that adjusts most appropriately to the nature of the image being projected, dimensions of the simulation unit, accounts for the magnification of the examination tool, and maximizes resolution is a biconcave lens with, for example, such as the following approximate dimensions: 12 mm diameter, central thickness of 3 mm, focal length of −12 mm, BFL of −12.81 mm and AR coating on both sides.

Figure 4:
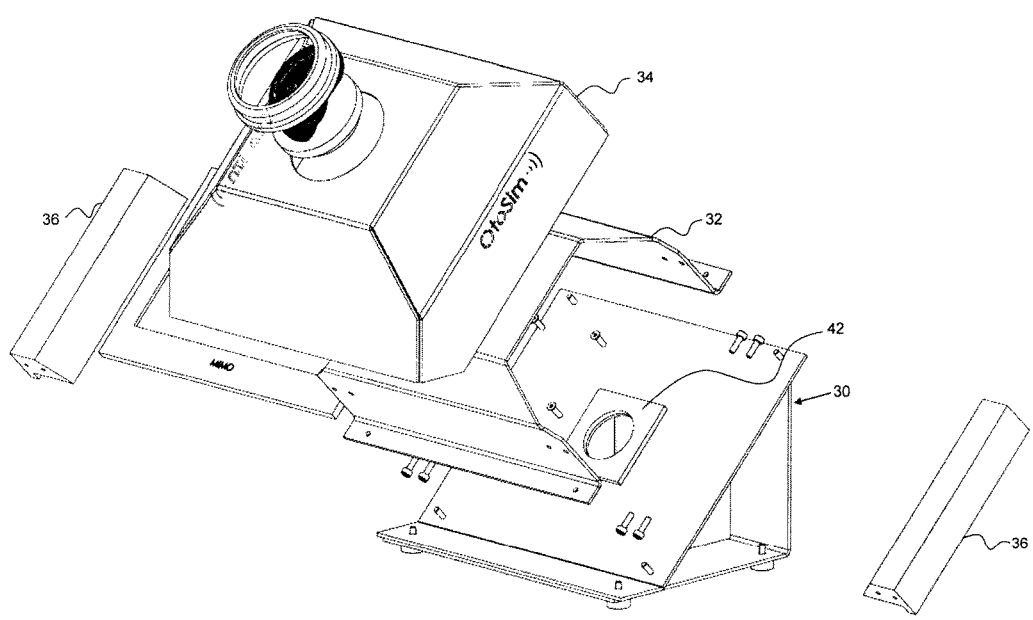
FIG. 4 is an exploded view of a representative embodiment of the medical training simulation apparatus of the present invention.

As shown in FIG. 4, for example, the apparatus may include a support frame 30, which may comprise a holder 42 that is operable to receive the video display and maintain the video display in place. Additional mounting means, for example, such as screws or clamps, may be used to hold the video display in place. An inner frame 32 may define the spaced apart relationship of the physical model and the video display. A lid 34 may be mounted onto the inner frame 32. The lid 34 may include an opening for receiving the physical model and incorporating the physical model in the apparatus.

An optional feature that may be included in embodiments of the present invention, such as is shown in FIG. 4, includes the light guides 36. The light guides may enable some of the light from the display to be directed to back illuminate a brand identifier cut out formed in the body of the apparatus. A rectangular acrylic prism shaped with three acute angles and one obtuse angle to enable light entering from the bottom surface to be internally reflected and emitted out from the opposite face may be optionally be included.

Figure 6:
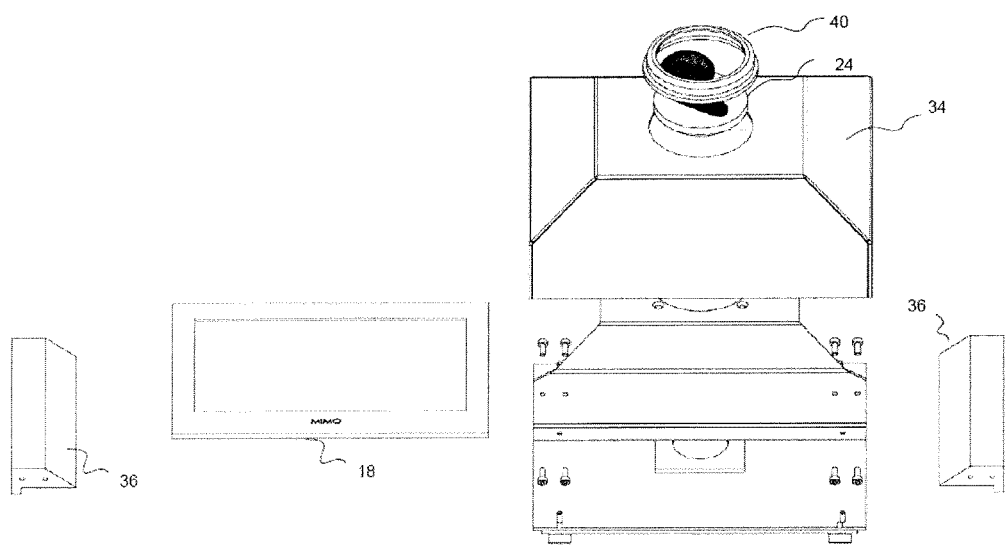
FIG. 6 is an exploded view of a representative embodiment of the medical training simulation apparatus of the present invention.

Multiple light guides 36 may be incorporated in an embodiment of the present invention, as shown in FIG. 6. The light guides may surround the video display 18, wholly or partially. The light guides may incorporate holes whereby the guides may be held in place in the apparatus by screws or other attachment means. A lid 34 may be mounted as a top portion of the apparatus. The lid 34 may include an opening for receiving the physical model 24 and incorporating the physical model in the apparatus. A retaining ring 40 may be utilized to removeably connect the physical model and incorporate it in the apparatus.

Figure 5:
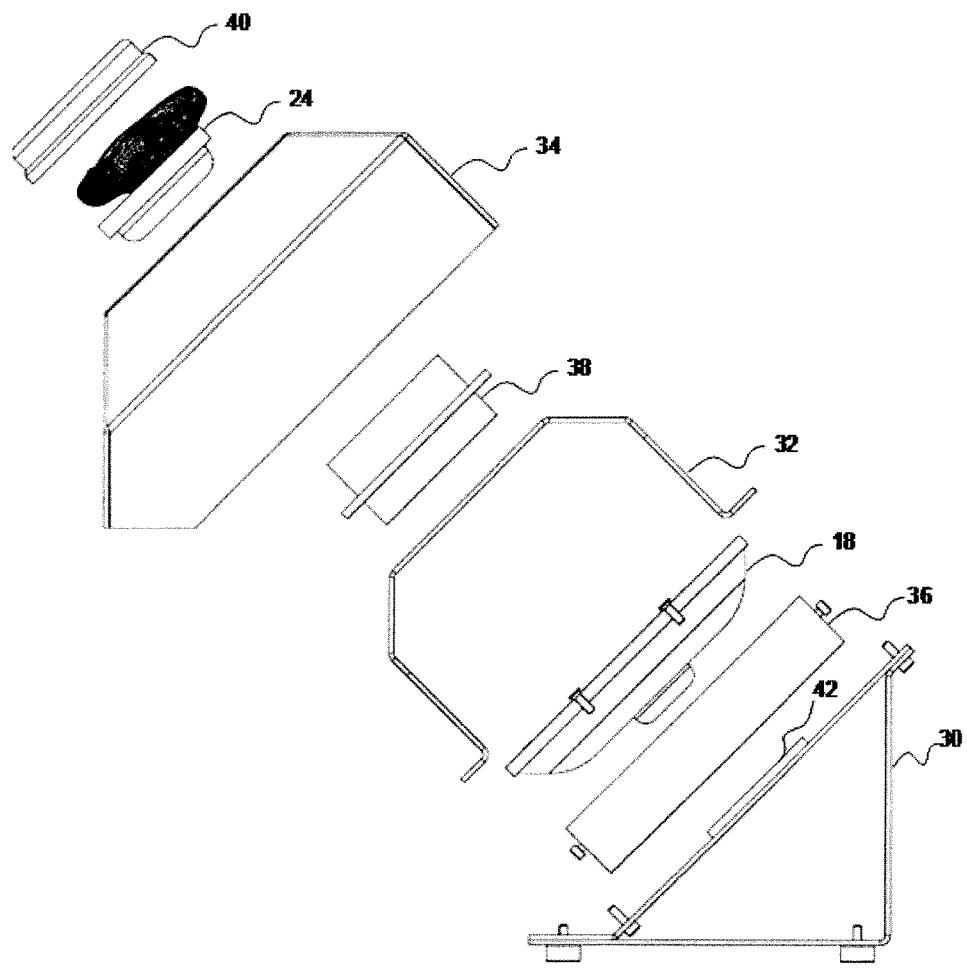
FIG. 5 is an exploded side view of a representative embodiment of the medical training simulation apparatus of the present invention.

As shown in FIG. 5, in another embodiment of the present invention a support frame 30, may comprise a holder 42 that is operable to receive the video display 18 and maintain the video display in place. A light guide 36 may be incorporated in the apparatus so as to surround wholly or partially the video display. An inner frame 32 may define the spaced apart relationship of the physical model and the video display, and also retain a lens holder 38. A lid 34 may be mounted onto the inner frame 32. The lid 34 may include an opening for receiving the physical model and incorporating the physical model in the apparatus. The opening may also receive the lens holder 38. As shown in FIG. 5, the lens holder 38 and a retaining ring 40 may co-operate to hold the lens and the physical model 24 in place, such that the opening referred to above and the video display are aligned, with the lens 26 disposed there between.

As shown in FIG. 7*a*, alternative configurations of embodiment of the present invention may be utilized to assemble the apparatus, so that a video display 48 is house between a support frame 52 and a top portion 46. Said top portion having a physical model 44 attachable thereto. The embodiment of the present invention shown in FIG. 7*a* notably does not incorporate light guides.

Figure 7B:
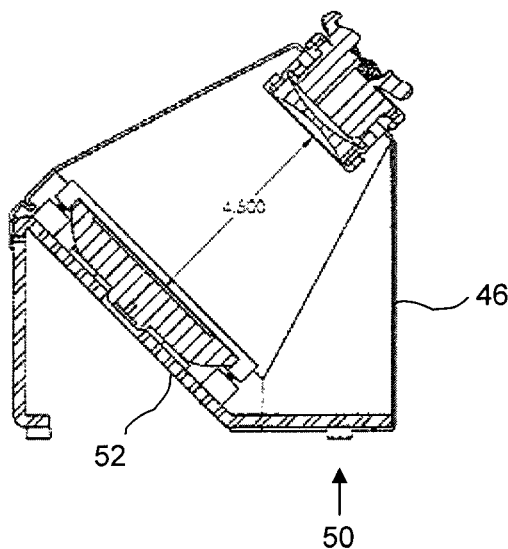
Figure 7C:
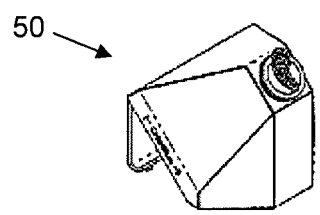
Figure 7D:
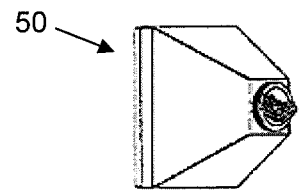
Figure 7E:
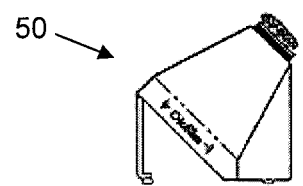
Figure 7F:
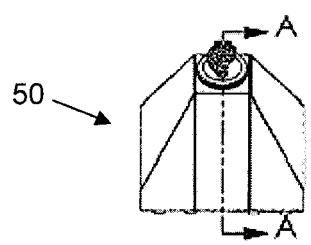

As shown in FIG. 7*b*, when assembled, an embodiment of the present invention apparatus 50 may be configured so that the support frame 52 is attached to the top portion 46. Views of an assembled embodiment of the present invention apparatus 50 are shown in FIGS. 7*c*, 7*d*, 7*e* and 7*f*.

Computer Implementation

The computer system, computer program, and computer implemented method aspects of the present may be practiced in various embodiments.

Figure 9:
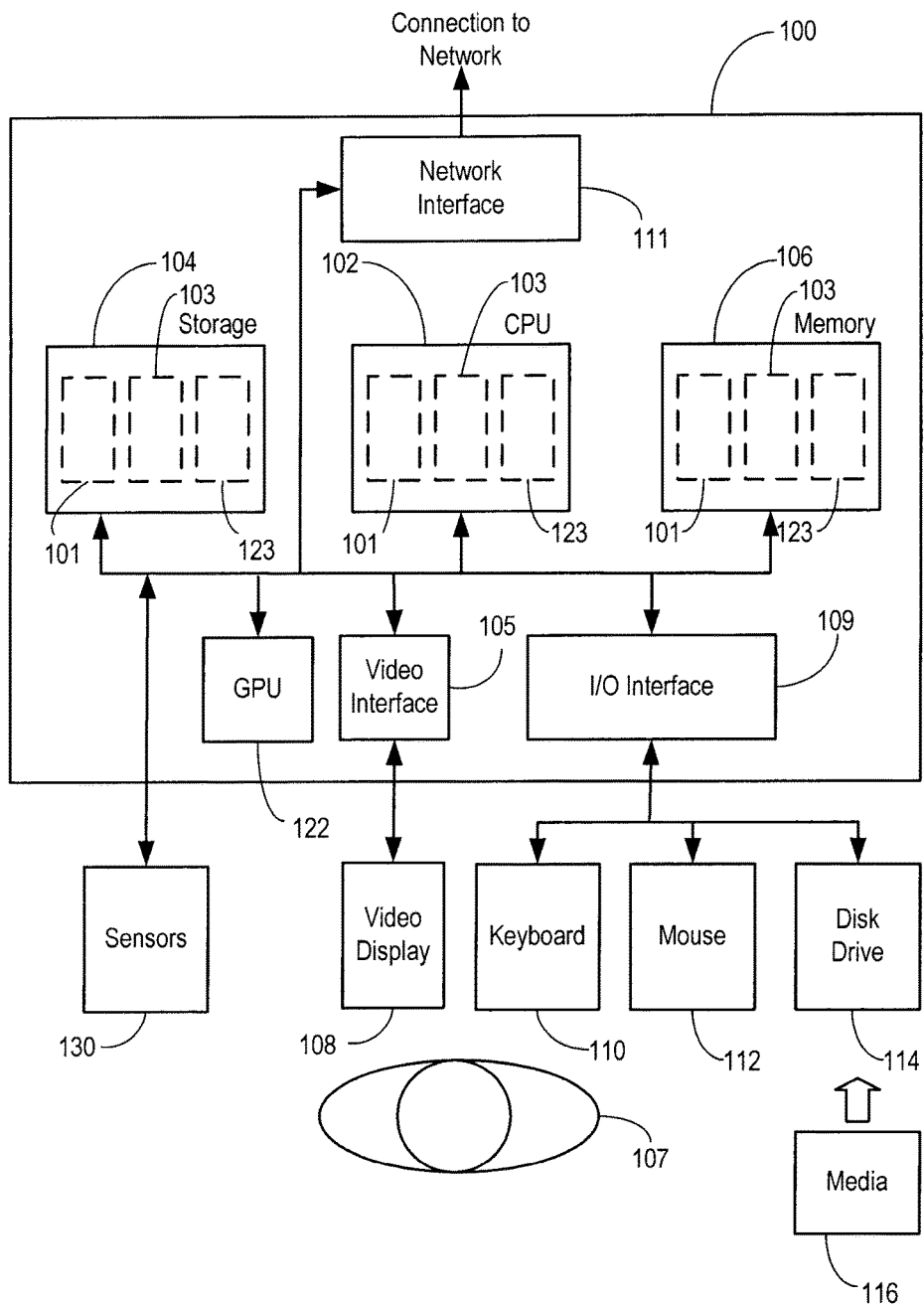
FIG. 9 illustrates a computer system for implementing the present invention.

A suitably configured computer device, and associated communications networks, devices, software and firmware, may provide a platform for enabling one or more embodiments as described above. A possible generic computer implementation is shown in FIG. 9. By way of example, it should be understood that computer may refer to a generic computer device that may include a central processing unit ("CPU") connected to a storage unit and to a random access memory. The CPU may process an operating system, application program, and data. The operating system, application program, and data may be stored in storage unit and loaded into memory, as may be required. Computer device may further include a graphics processing unit (GPU) which is operatively connected to CPU and to memory to offload intensive image processing calculations from CPU and run these calculations in parallel with CPU. An operator may interact with the computer device using a video display connected by a video interface, and various input/output devices such as a keyboard, mouse, and disk drive or solid state drive connected by an I/O interface. In known manner, the mouse may be configured to control movement of a cursor in the video display, and to operate various graphical user interface (GUI) controls appearing in the video display with a mouse button. The disk drive or solid state drive may be configured to accept computer readable media. The computer device may form part of a network via a network interface, allowing the computer device to communicate with other suitably configured data processing systems (not shown). One or more different types of sensors may be used to receive input from various sources.

The present system and the computer implemented methods described may be practiced on virtually any manner of computer device including a desktop computer, laptop computer, tablet computer, provided that optimal processing, memory and other hardware/software requirements are met. The present system and method may also be implemented as a computer-readable/useable medium that includes computer program code to enable one or more computer devices to implement each of the various process steps in a method in accordance with the present invention. It is understood that the terms "computer-readable medium" and "computer useable medium" comprises one or more of any type of physical embodiment of the program code. In particular, the computer-readable/useable medium can comprise program code embodied on one or more portable storage articles of manufacture (e.g. an optical disc, a magnetic disk, a tape, etc.), on one or more data storage portioned of a computing device, such as memory associated with a computer and/or a storage system.

Other Implementations

A skilled reader will recognize that numerous implementations of the technology of the present invention are possible.

For example, embodiments of the present invention may include various sensors whereby aspects of the simulated medical examination or procedure undertaken by the trainee using the apparatus may be collected. The sensors may be chosen and positioned so as to gather information regarding aspects of the simulated medical examination or procedure such as relating to the patient experience of the medical examination or procedure, relating to aspects of use of the medical tool by the trainee, or other aspects of the process of the trainee's hands-on experience of use of the simulated body part and the use of the appropriate medical tool.

For example, an embodiment of the present invention may be extended to provide haptic feedback to the user, for example by incorporating one or more haptic devices in the physical structure of the apparatus of the present invention. For example, the physical model may be constructed so as to trigger an alarm if a user touches a sensitive area of a body part or manipulates the body part in a way that is not desired (e.g. pulls on the ear too hard, or comes into contact with a portion of the surface of the ear canal that given a defect for example is particularly sensitive). The alarm may consist of auditory feedback or vibration of the physical model, or some other signal.

As another example, the physical model of an embodiment of the present invention may be constructed to include a sensor array (for example covering the inner surfaces of the physical model, or a portion thereof, such as the simulated ear canal or other body part represented by the physical model). The sensitivity of the sensors in the array may be configured, working with clinicians, to correspond to the sensitivity of the body part in specific areas thereof. In a further aspect of the invention, a sensor array profile may be associated with each image, as the sensitivity of a body part may vary depending on the particular defect or medical condition. For example, force feedback sensors could be used such that once a user brings the medical examination tool into contact with a specific sensor, in a particular area of the physical model, and expresses with the medical examination tool a force that exceeds a specific threshold, an alarm or other feedback mechanism may be triggered.

In another embodiment of the present invention, the physical model may be impregnated with a combination of torque and pressure sensors in the helix, scapha and fossa *triangularis* regions of the outer ear model. The pressure sensors may provide a feedback signal following detection of excessive force exerted by the trainee during use of the medical examination tool. High acuity force-pressure sensors may be placed below the surface of the canal region of the physical model, for example, such as approximately 1.5 mm, to enable sensing of excessive force. Vibrations and noise may be emitted from the unit when excessive force is exerted on any regions of the physical model. To this end the apparatus of such embodiments of the present invention may incorporate a speaker or other sound emitter means.

The haptic and feedback mechanisms described above that may be incorporated into the physical models use in embodiments of the present invention, may enable more accurate simulation of real clinical scenarios.

A skilled reader will further recognize that the structure of embodiment of the medical training simulation apparatus of the present invention may be altered for telescopic viewing or three-dimensional viewing.

We claim:

1. A medical training system for simulating pneumatic otoscopy comprising: (a) a computer system linked to at least one base unit; (b) the base unit including or receiving one or more physical models of an outside of an ear, the physical model including an opening, and the base unit including one or more components that define a structure that simulates concealed geometry of the ear, the opening being configured to enable a trainee to insert a pneumatic otoscope through the opening and into the structure, the pneumatic otoscope including a lens and an apparatus for applying pressure to the inside of the ear (pressure applicator); (c) the one or more components including a video display that is controllable by the computer system, using a video controller, to display a series of medical images relating to the inside of an ear, such that when the trainee looks through the lens of the pneumatic otoscope, viewing the interior of the structure through the lens simulates the appearance of the interior of the ear; and (d) a tracker that tracks movements of the pneumatic otoscope made by the trainee, including movements of the pressure applicator, the tracker providing information to the video controller so as to adapt the one or more images displayed by the video display based on the tracked movements of the pneumatic otoscope, so as to simulate appearance of the interior of the ear when operating the pneumatic otoscope in conduct an ear examination, including using the pressure applicator.

2. The medical training system of claim 1, wherein the one or more medical images include images that show a tympanic membrane of an ear drum in different states based on application of pressure using a pneumatic otoscope.

3. The medical training system of claim 1, wherein the system is configured to train the trainee to generate a correct spectrum of pressure to test the mobility of the tympanic membrane of the ear drum, without harming a patient.

4. The medical training system of claim 1, wherein the one or more images include images of the inside of an ear presenting a medical condition, and the medical training system is configured to train the trainee to identify the condition using a pneumatic otoscope.

5. The medical training system of claim 1, wherein the pneumatic otoscope is a modified pneumatic otoscope that is operatively connected to the base unit.

6. The medical training system of claim 1, wherein: (a) the medical images consist of one or more groups of images, wherein each group of images depicts the concealed geometry of an ear across a series of movements involved in conducting an examination using a pneumatic otoscope, wherein individual images are indexed to particular movements of the pneumatic otoscope in connection with an ear examination using the pneumatic otoscope, and wherein the group of images represents the appearance of an ear across a spectrum of pressure generated using the pressure applicator; and (b) the tracker sends information to the computer system, and in response the computer system iteratively retrieves and directs the video controller to display the image corresponding to a particular movement tracked by the tracker, such that across a series of iterations, a series of images are displayed that simulate the appearance of the interior of the ear based on the particular movements of the trainee using the pneumatic otoscope in connection with conducting an ear examination on a human subject.

7. The medical training system according to claim 1, wherein the system includes a pressure sensor unit that tracks the modulation of pressure by the trainee using the pressure applicator.

8. A medical training system according to claim 6 or 7, wherein each image includes a frame, and each frame is mapped to a pressure value within a range of defined pressure, wherein based on pressure expressed using the pressure applicator, and sensed by the pressure sensor unit, a real time or near real time pressure value is identified (based on use of the pneumatic otoscope by the trainee in connection with an ear examination using the pneumatic otoscope) and the corresponding frame is retrieved and displayed by the video display.

9. A medical training system as claimed in claim 1, wherein: (a) one or more base units are networked; and (b) one or more computer systems execute programming that include an ear examination training module, wherein the ear examination training module may be used to control the images displayed on the respective video displays of the one or more base units.

10. The medical training system of claim 8, wherein a trainer module is executed by the one or more computer systems, and the trainer module selectively controls the images displayed by the respective one or more base units, including based on one or more pneumatic otoscopy lesson modules, and the one or more of the base units include a monitoring module that is used to monitor the performance of trainee(s) using each base unit, and associated performance data is logged by the trainer module for trainee assessment and reporting.

11. The medical training system of claim 8, wherein the system enables the trainee to learn to manipulate a pneumatic otoscope properly and to observe the results of manipulation of the pneumatic otoscope on an ear canal.

12. The medical training system of claim 1, wherein the physical model is formed so that, when used properly, the trainee can generate a seal between the pneumatic otoscope and the physical model of the ear.

13. A computer implemented medical training method for learning to conduct a medical examination using a pneumatic otoscope comprising: (a) one or more users engaging a simulation computer system to initiate an ear examination training routine, by means of one or more computer processors, the simulation computer system including: (i) a video display disposed within a base unit that includes a physical model of an outside of an ear, the physical model including an opening, and the base unit including one or more components that define a structure that simulates concealed geometry of the ear; (ii) a pneumatic otoscope including a lens and a pressure applicator; (iii) a database including a series of medical images that show the inside of an ear, where each image corresponds to the appearance of the inside of an ear in connection application of particular pressure using the pressure applicator; and (iv) a controller for controlling the video display to selective display the medical images; wherein, the opening is configured to enable a trainee to insert a pneumatic otoscope through the opening and into the structure, and view an interior of the structure through the lens; (b) one or more of the users who are trainee users inserting the pneumatic otoscope into the opening, and using the pressure applicator so as to apply pressure as is done in conducting an ear examination using a pneumatic otoscope; (c) tracking the pressure applied using the pressure applicator based on a series of pressure values; (d) selectively retrieving and displaying to the video display medical images corresponding to the series of pressure values, thereby simulating the appearance of the interior of the ear during an ear examination when the trainee users view the interior of the structure through the lens.

14. The method of claim 13, wherein the physical model is formed to enable a seal to be made between the pneumatic otoscope and the physical model, and comprising the step of generating a seal between the pneumatic otoscope and the physical model so as to generate vacuum/pressure in the interior of the structure.

15. The method of claim 13 comprising generating a feedback message based on the performance of a trainee user based on one or more training parameters.

16. The method of claim 15 comprising communicating feedback information to a trainee user based on their performance relative to the training parameters.

17. The method of claim 13, wherein the one or more medical images include images that show a tympanic membrane of an ear drum in different states based on application of pressure using a pneumatic otoscope.

18. The method of claim 13, wherein the method is adapted to train the one or more trainee users to generate a correct spectrum of pressure to test the mobility of the tympanic membrane of the ear drum, without harming a patient.

19. The method of claim 13, wherein the one or more images include images of the inside of an ear presenting a medical condition, and the method is adapted to train the one or more trainee users to identify the condition using a pneumatic otoscope.

\* \* \* \* \*